United States Patent
Propper et al.

(10) Patent No.: US 9,944,994 B2
(45) Date of Patent: Apr. 17, 2018

(54) ANURAN CROSS-SPECIES MOLECULAR SENSORS

(71) Applicant: Arizona Board of Regents acting for and on behalf of Northern Arizona University, Flagstaff, AZ (US)

(72) Inventors: Catherine R. Propper, Flagstaff, AZ (US); Stephen M. Beckstrom-Sternberg, Phoenix, AZ (US); Caren C. Helbing, Victoria (CA); Nicholas J. Veldhoen, Victoria (CA)

(73) Assignee: Arizona Board of Regents on Behalf of Northern Arizona University, Flagstaff, AZ (US)

( * ) Notice: Subject to any disclaimer, the term of this patent is extended or adjusted under 35 U.S.C. 154(b) by 0 days.

(21) Appl. No.: 15/234,715

(22) Filed: Aug. 11, 2016

(65) Prior Publication Data
US 2016/0340747 A1 Nov. 24, 2016

Related U.S. Application Data

(62) Division of application No. 14/507,832, filed on Oct. 7, 2014, now Pat. No. 9,448,227.

(60) Provisional application No. 61/883,138, filed on Sep. 26, 2013.

(51) Int. Cl.
*C12Q 1/68* (2006.01)
*G01N 33/50* (2006.01)
*G01N 33/78* (2006.01)

(52) U.S. Cl.
CPC ......... *C12Q 1/6888* (2013.01); *C12Q 1/6851* (2013.01); *C12Q 1/6883* (2013.01); *G01N 33/5014* (2013.01); *G01N 33/5088* (2013.01); *G01N 33/78* (2013.01); *C12Q 2600/142* (2013.01); *C12Q 2600/158* (2013.01); *C12Q 2600/16* (2013.01); *G01N 2333/4606* (2013.01); *G01N 2520/00* (2013.01)

(58) Field of Classification Search
None
See application file for complete search history.

(56) References Cited

PUBLICATIONS

Skirrow et al., Developmental Dynamics vol. 237 (2008) pp. 3787-3797.

*Primary Examiner* — James S Ketter
(74) *Attorney, Agent, or Firm* — Gavin J. Milczarek-Desai; Quarles & Brady LLP

(57) ABSTRACT

Described herein are DNA primer sequences designed for the determination of gene or transcript information from Anuran species, and which may be used in studies for developmental and/or toxicity testing and for environmental toxicology or ecological assessment. Also described herein is a rapid, sensitive, high-throughput assay useful for supporting potential risk assessment across vertebrate clades, and that is also useful for evaluation of complex contaminant mixtures.

4 Claims, 37 Drawing Sheets

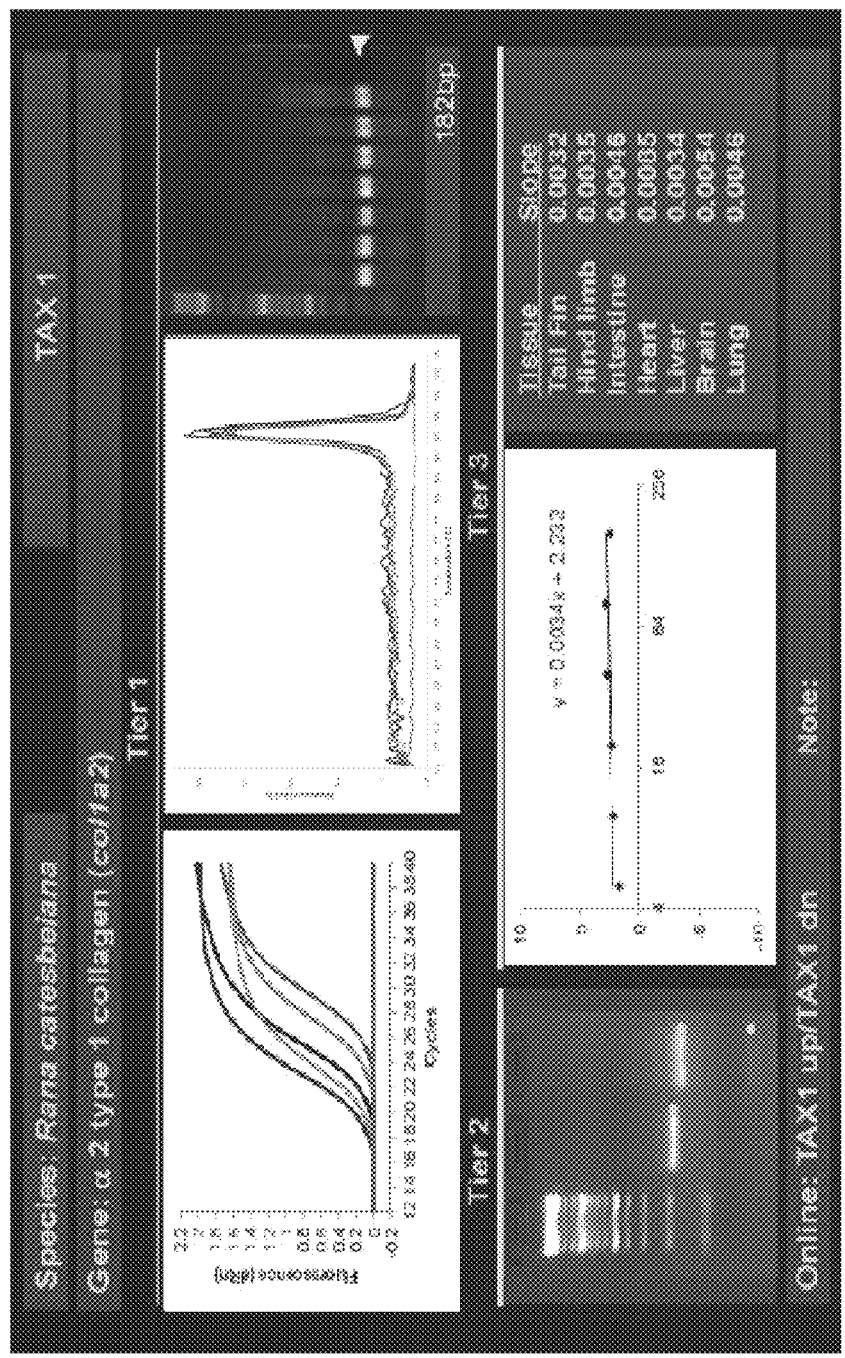
FIG. 2A(1)

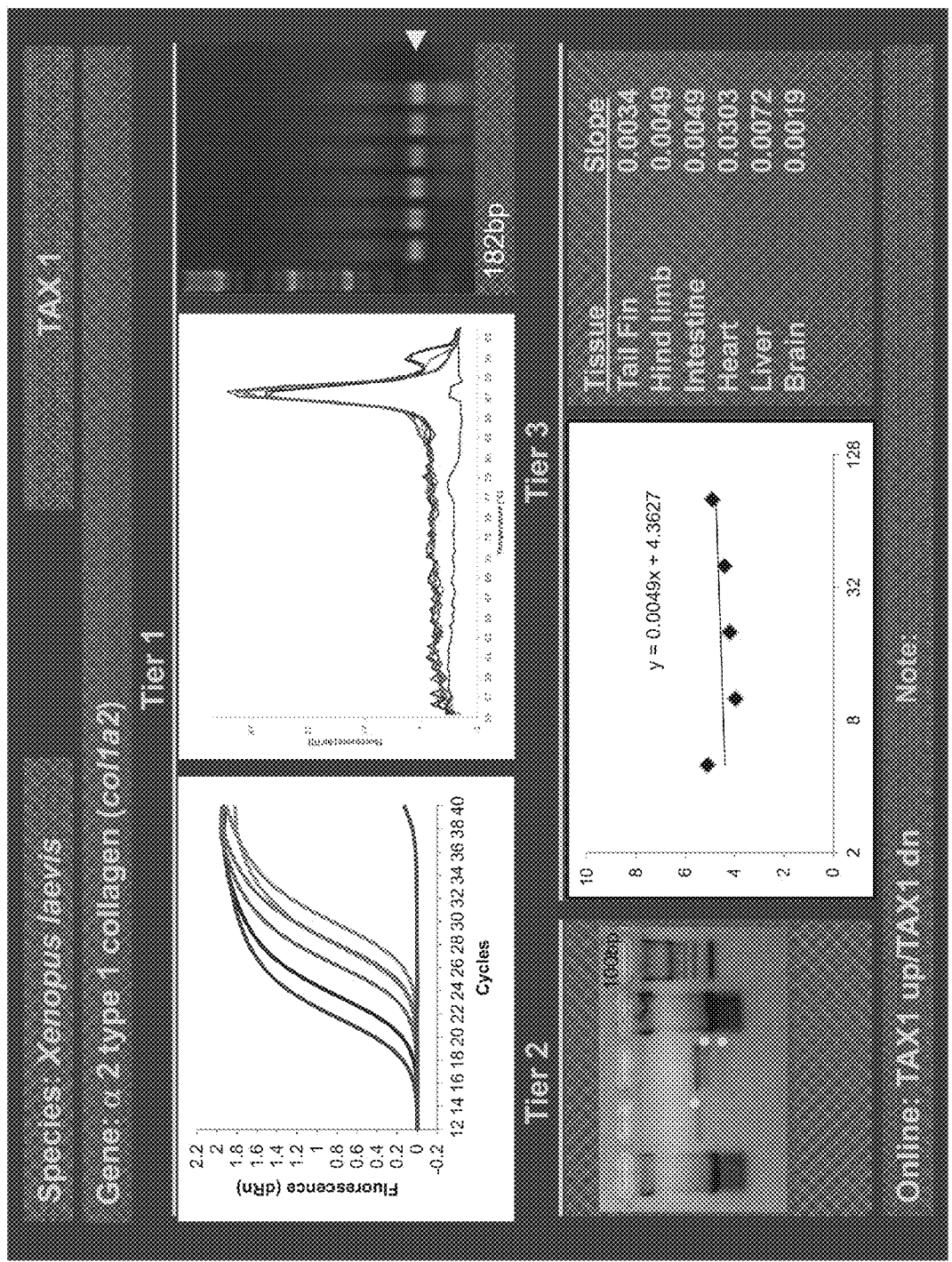
FIG. 2A(2)

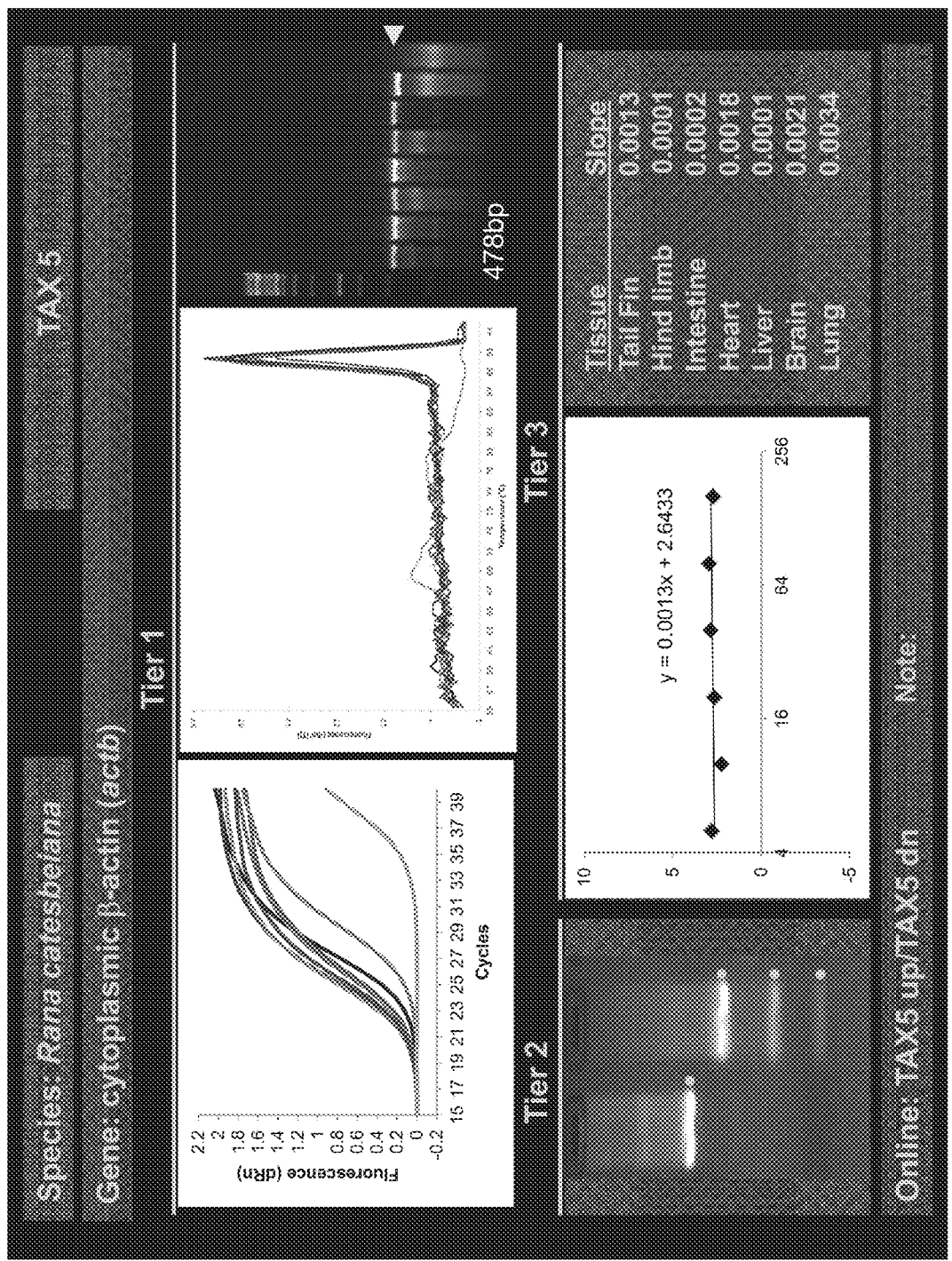
FIG. 2A(3)

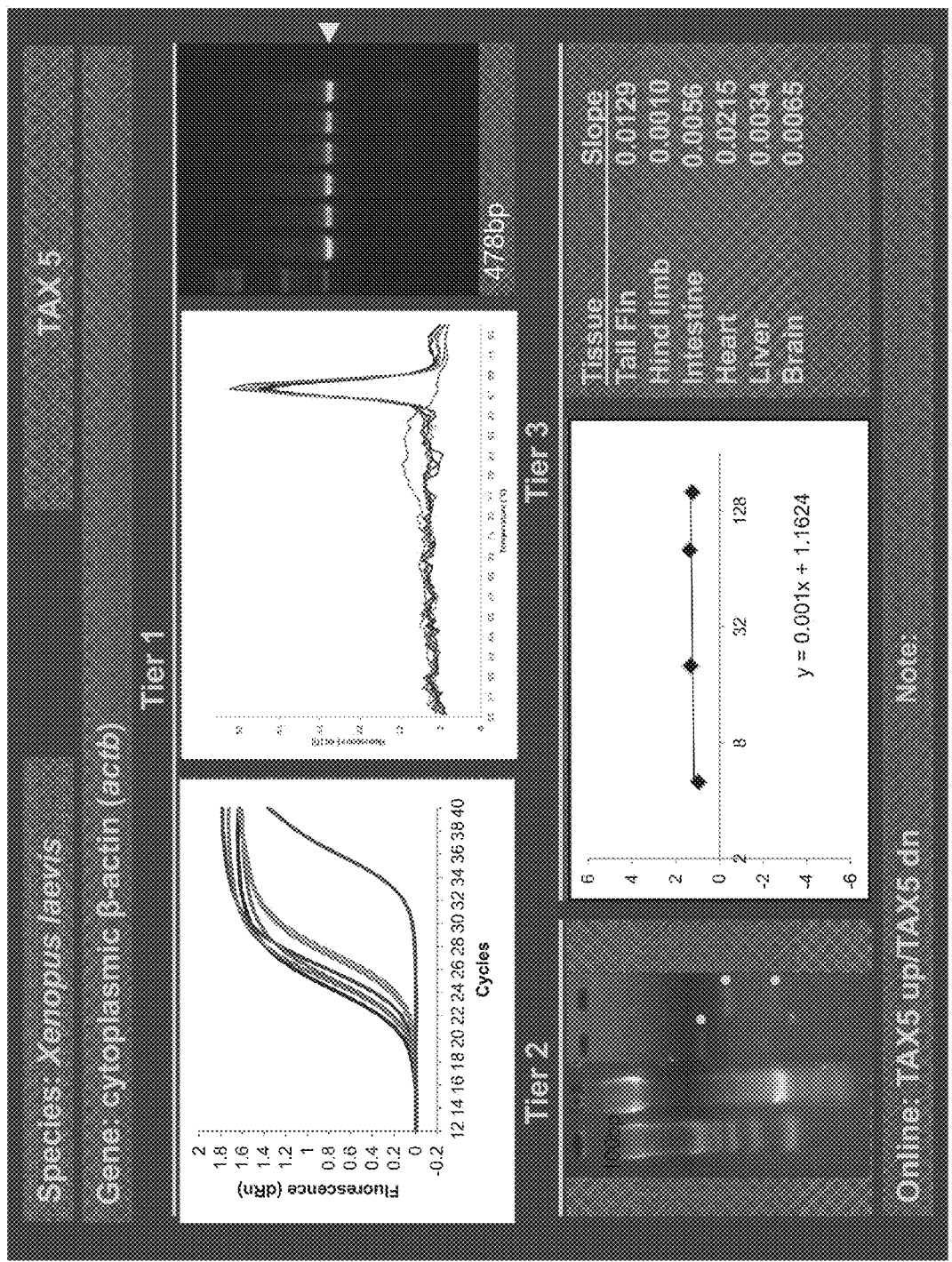
FIG. 2A(4)

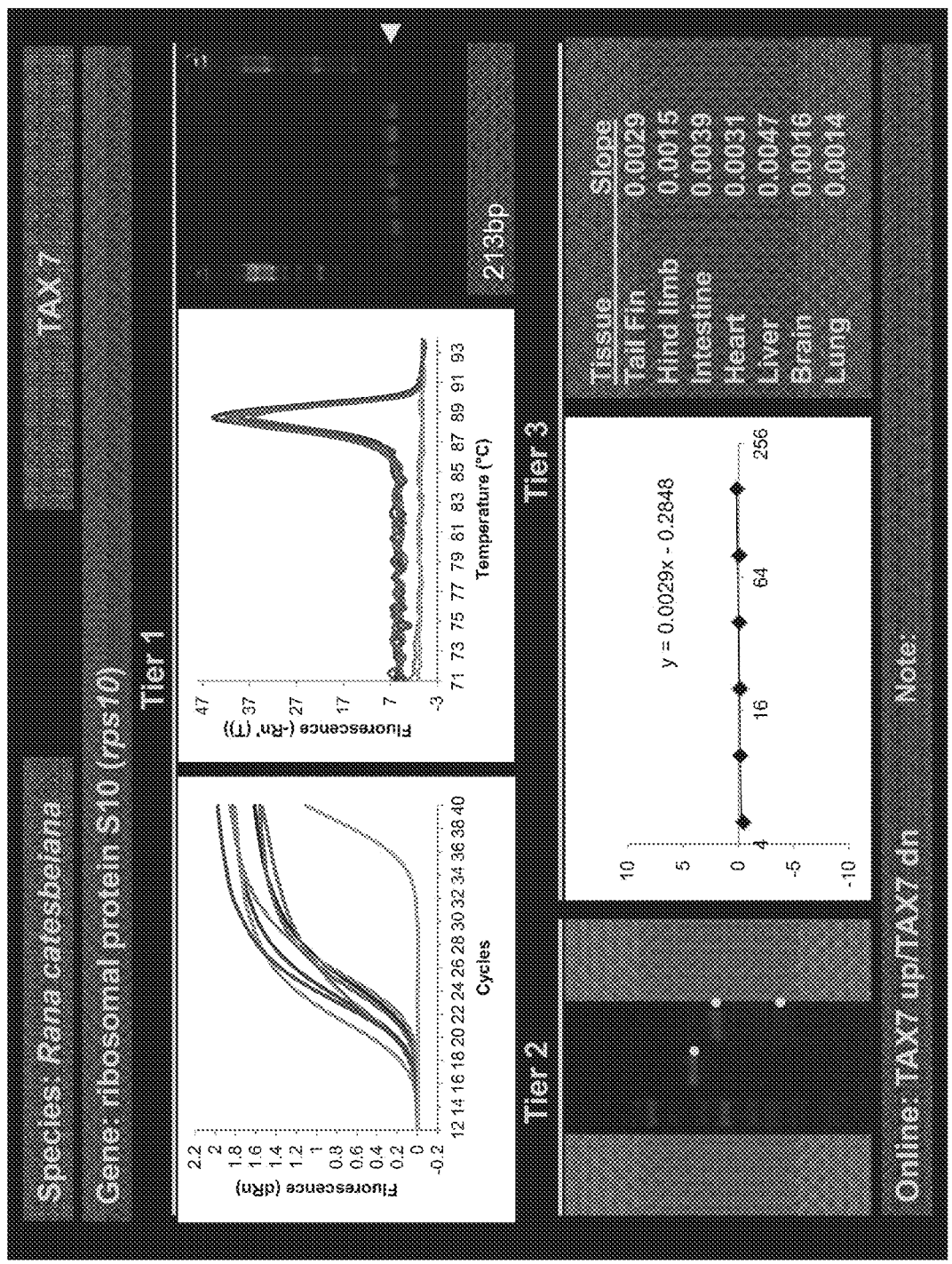
FIG. 2A(5)

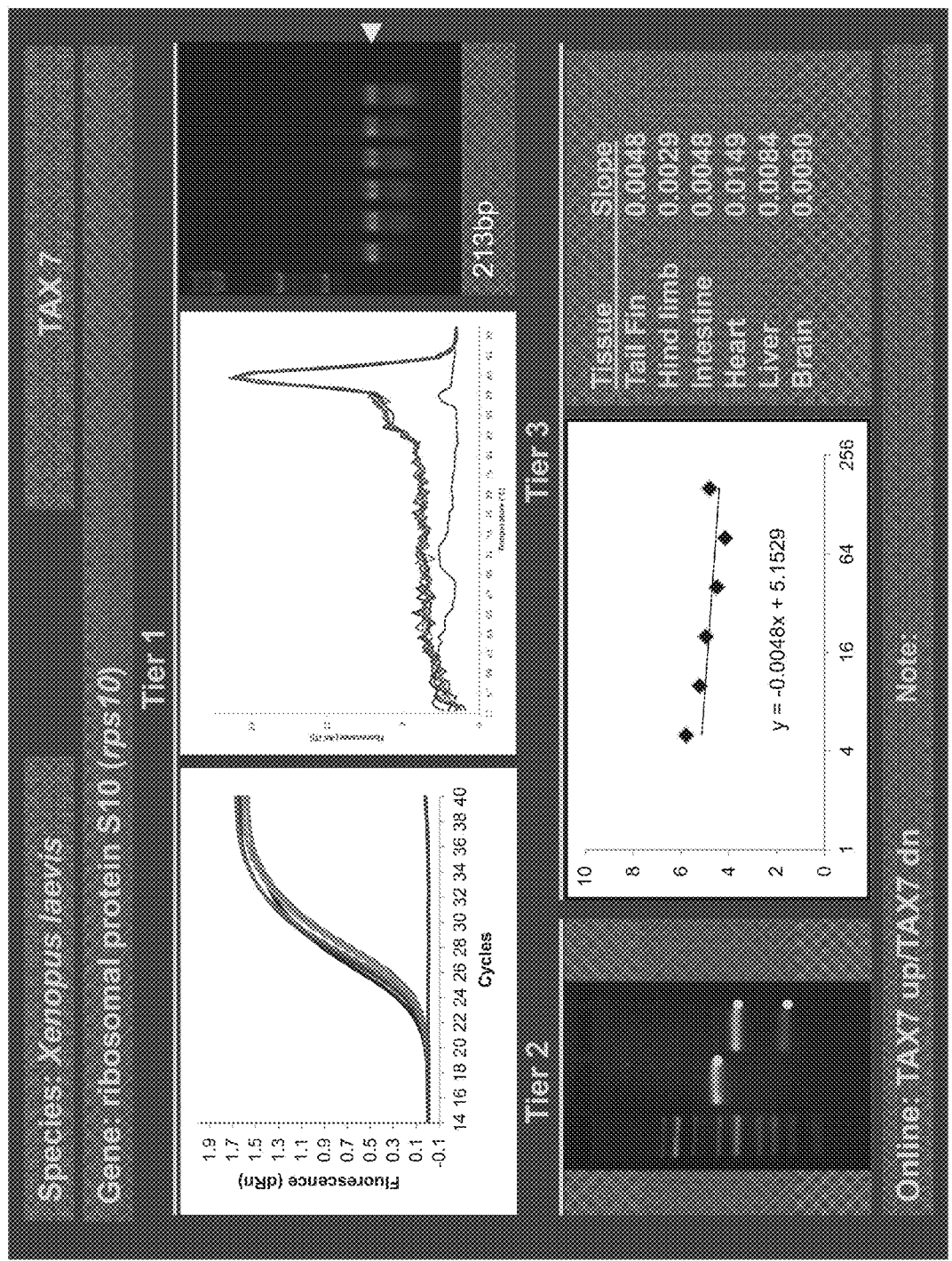
FIG. 2A(6)

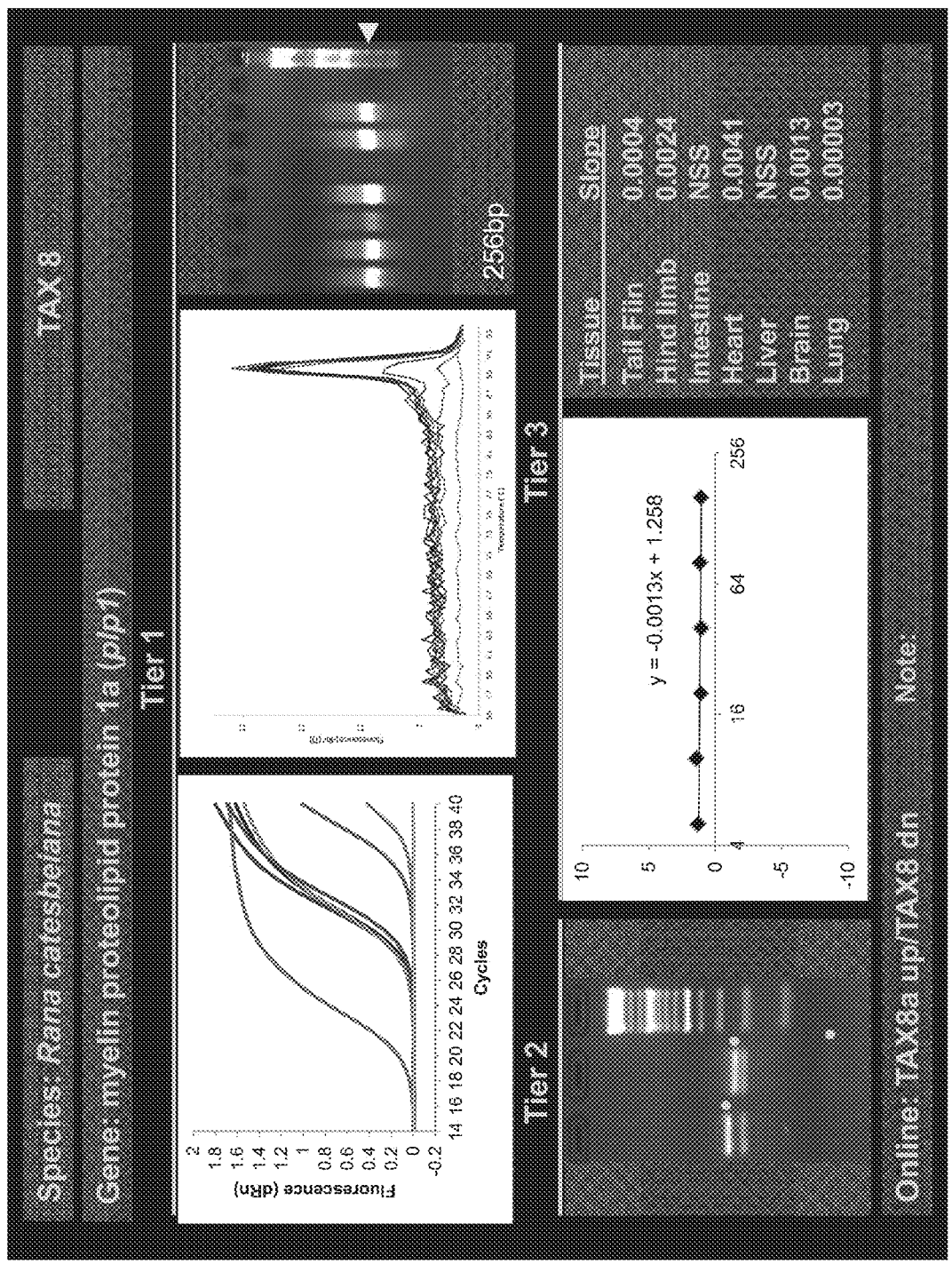
FIG. 2A(7)

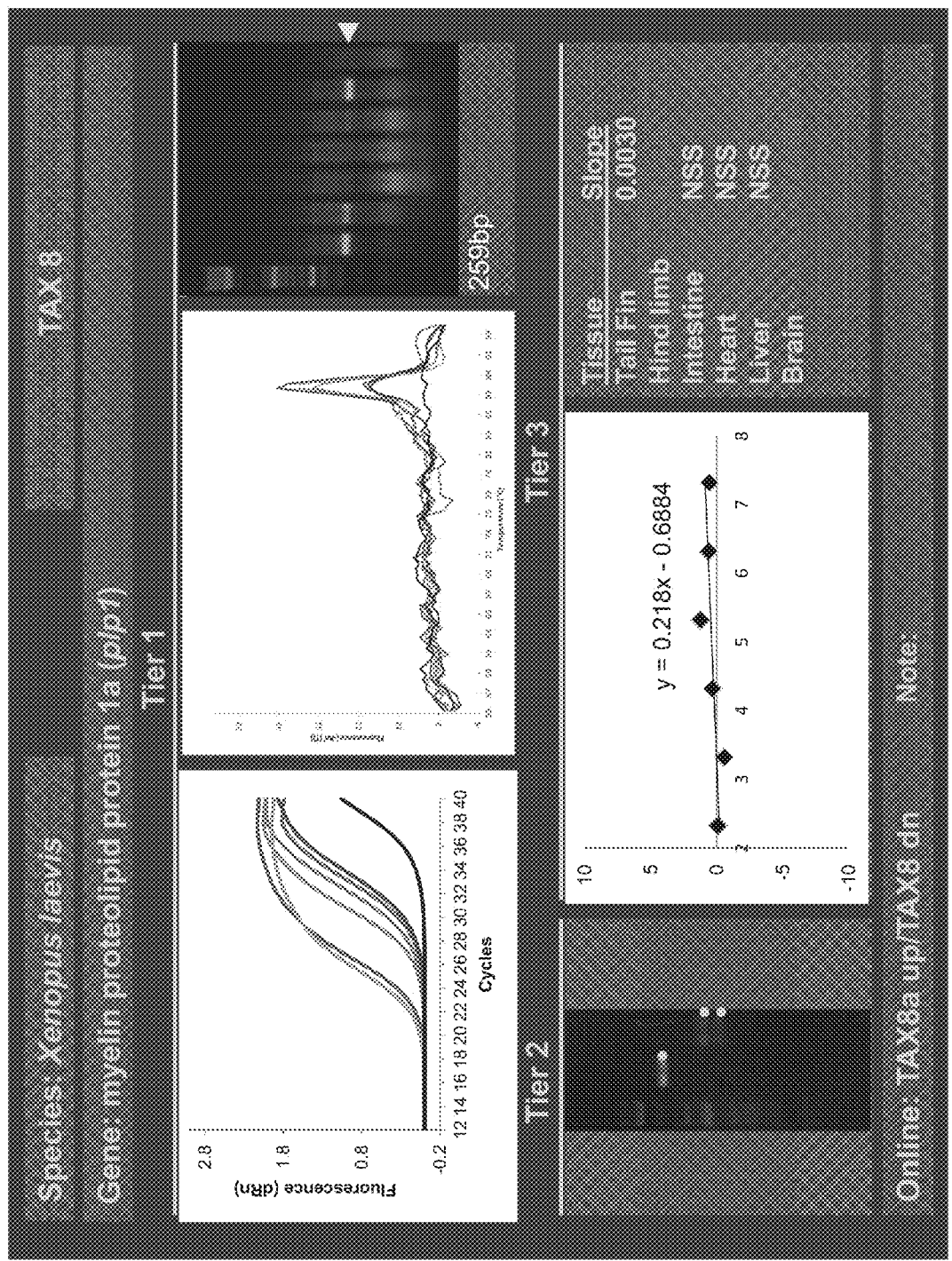
FIG. 2A(8)

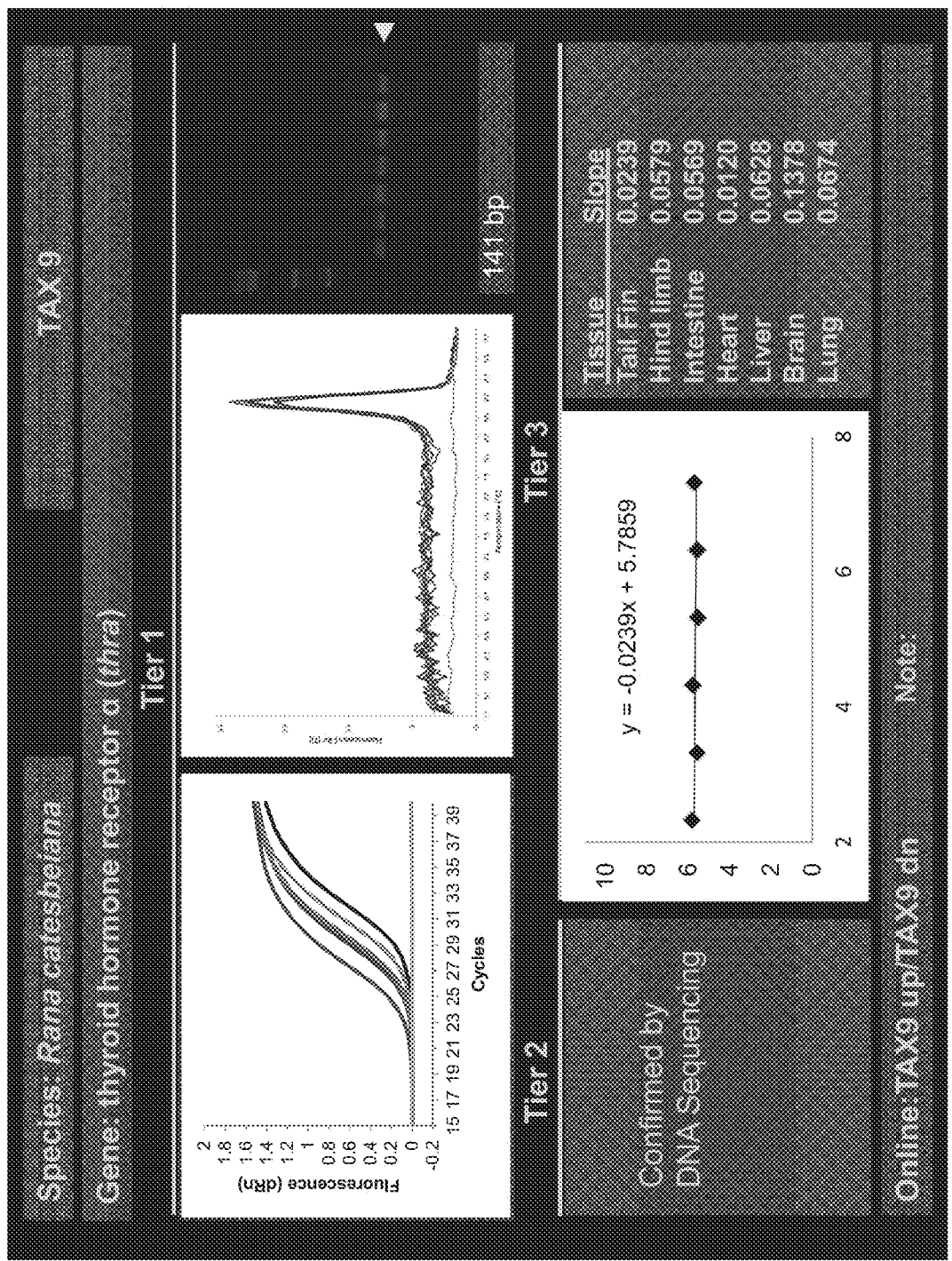
FIG. 2A(9)

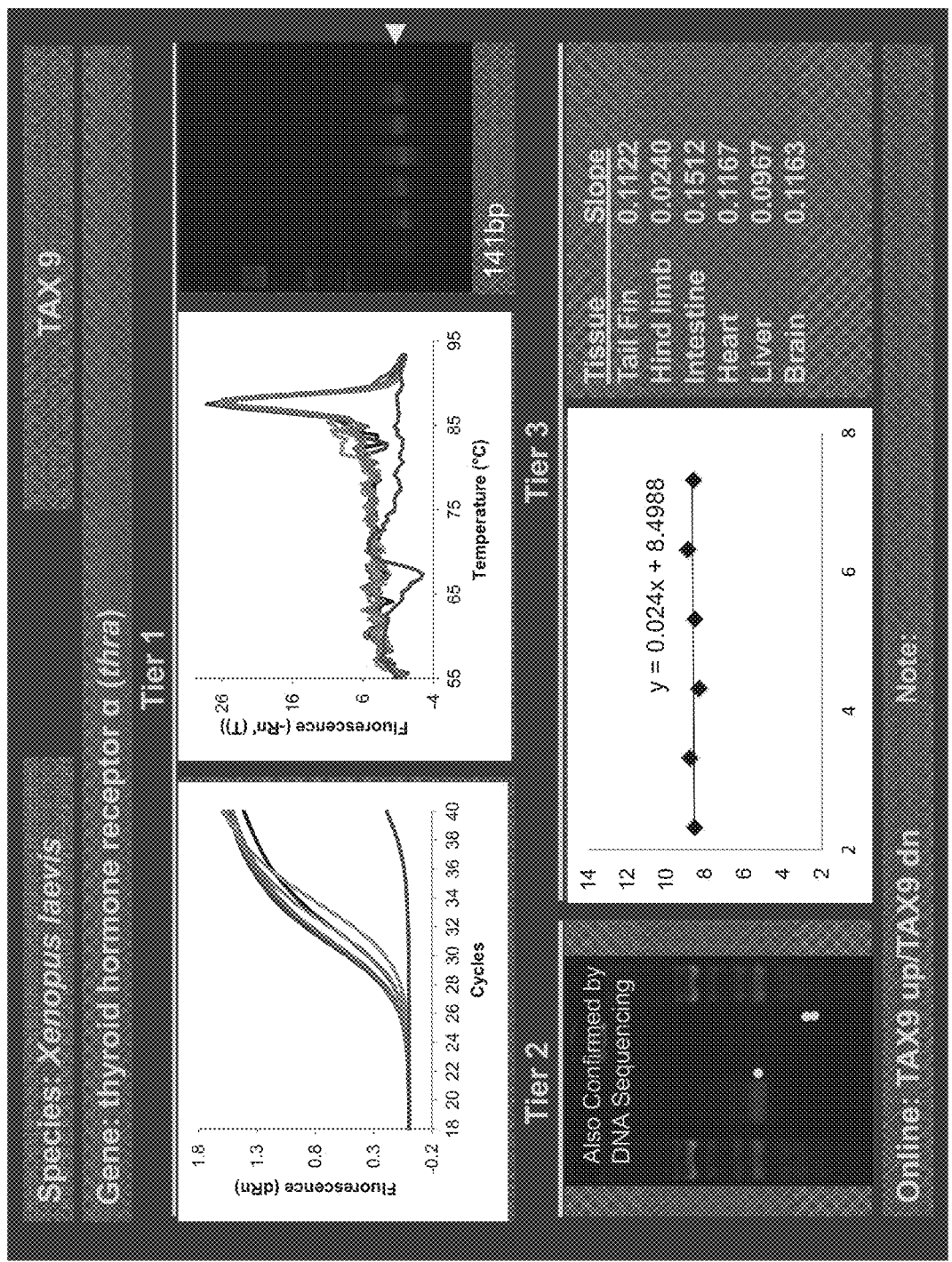
FIG. 2A(10)

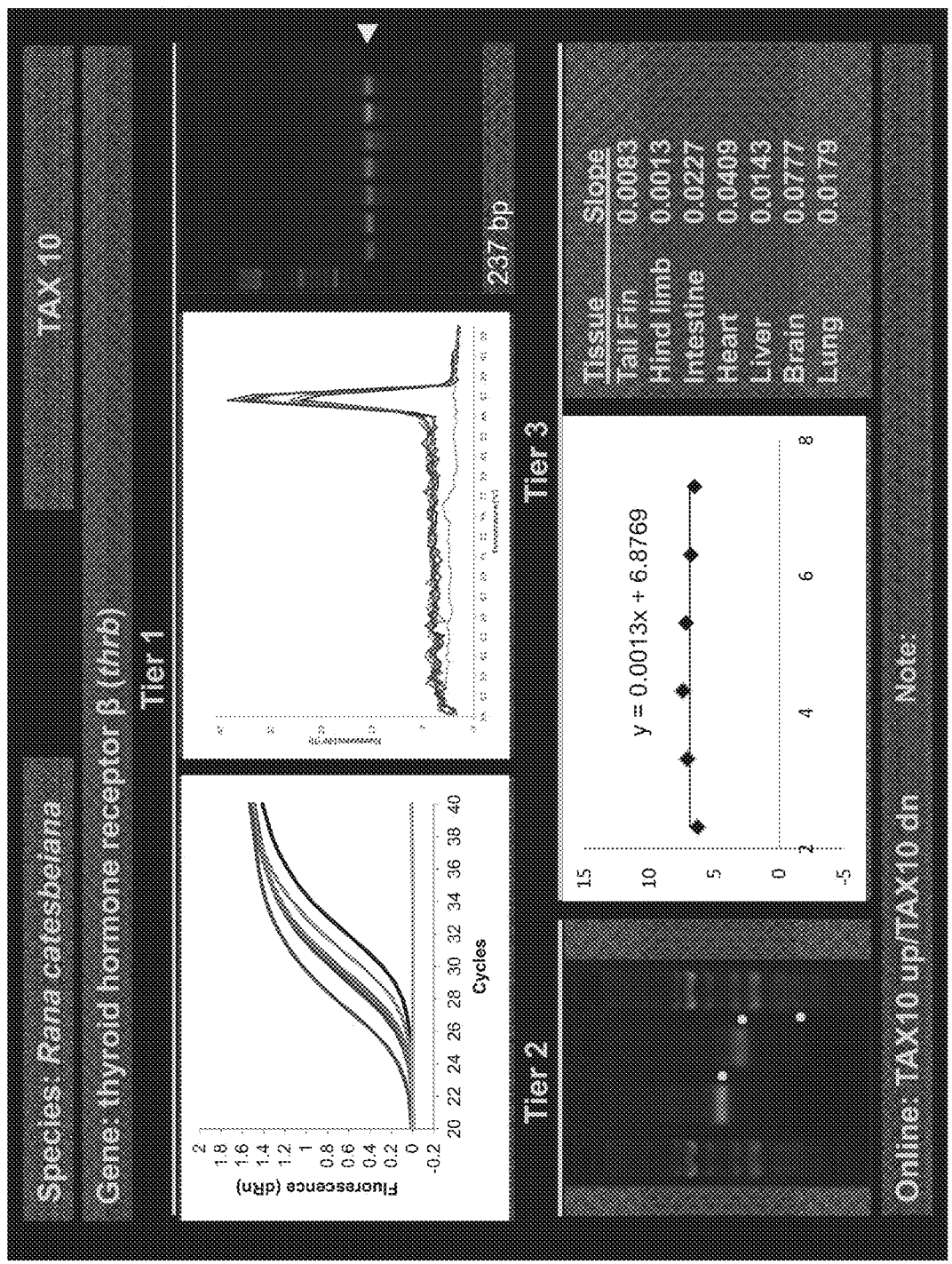
FIG. 2B(1)

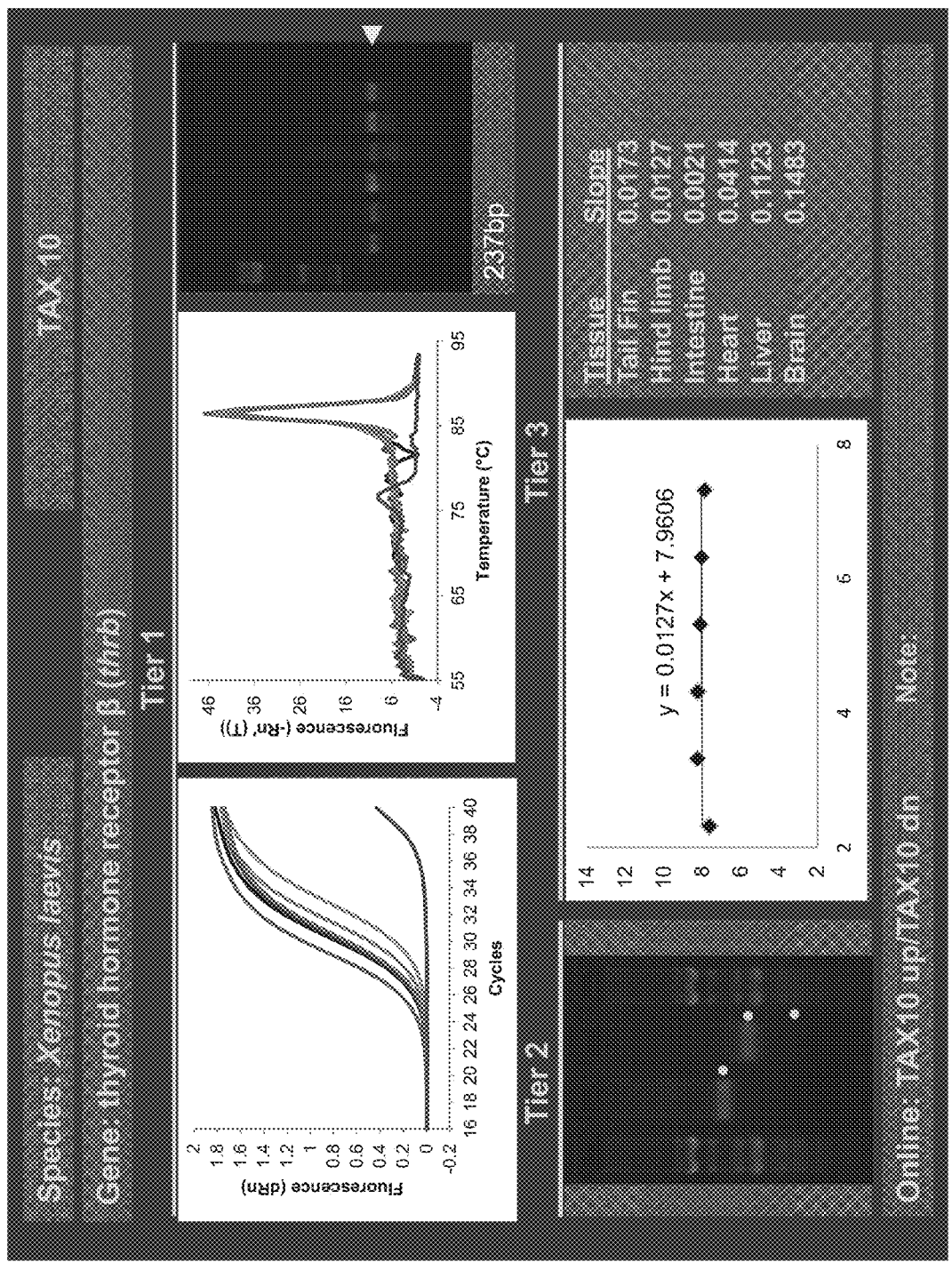
FIG. 2B(2)

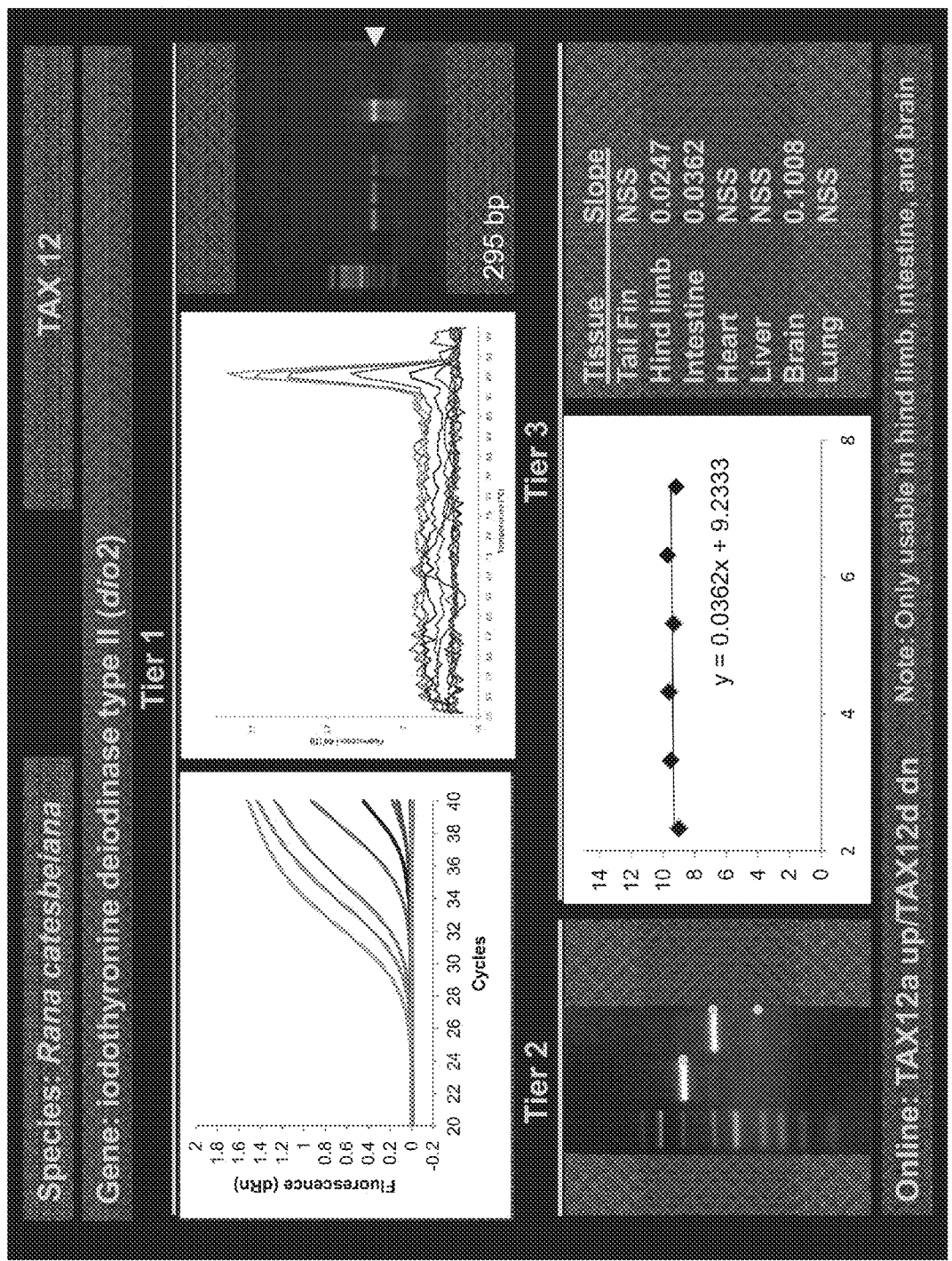
FIG. 2B(3)

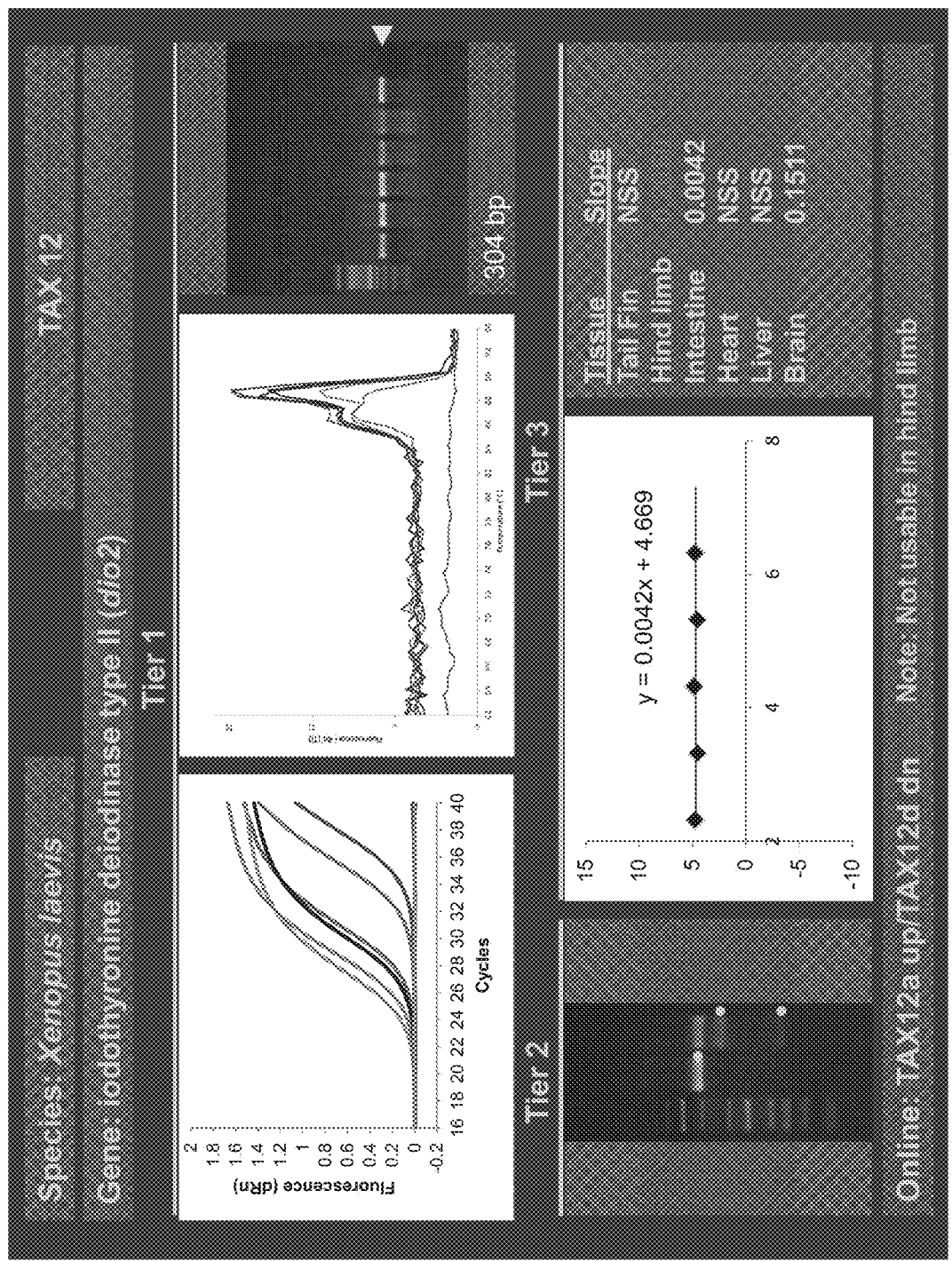
FIG. 2B(4)

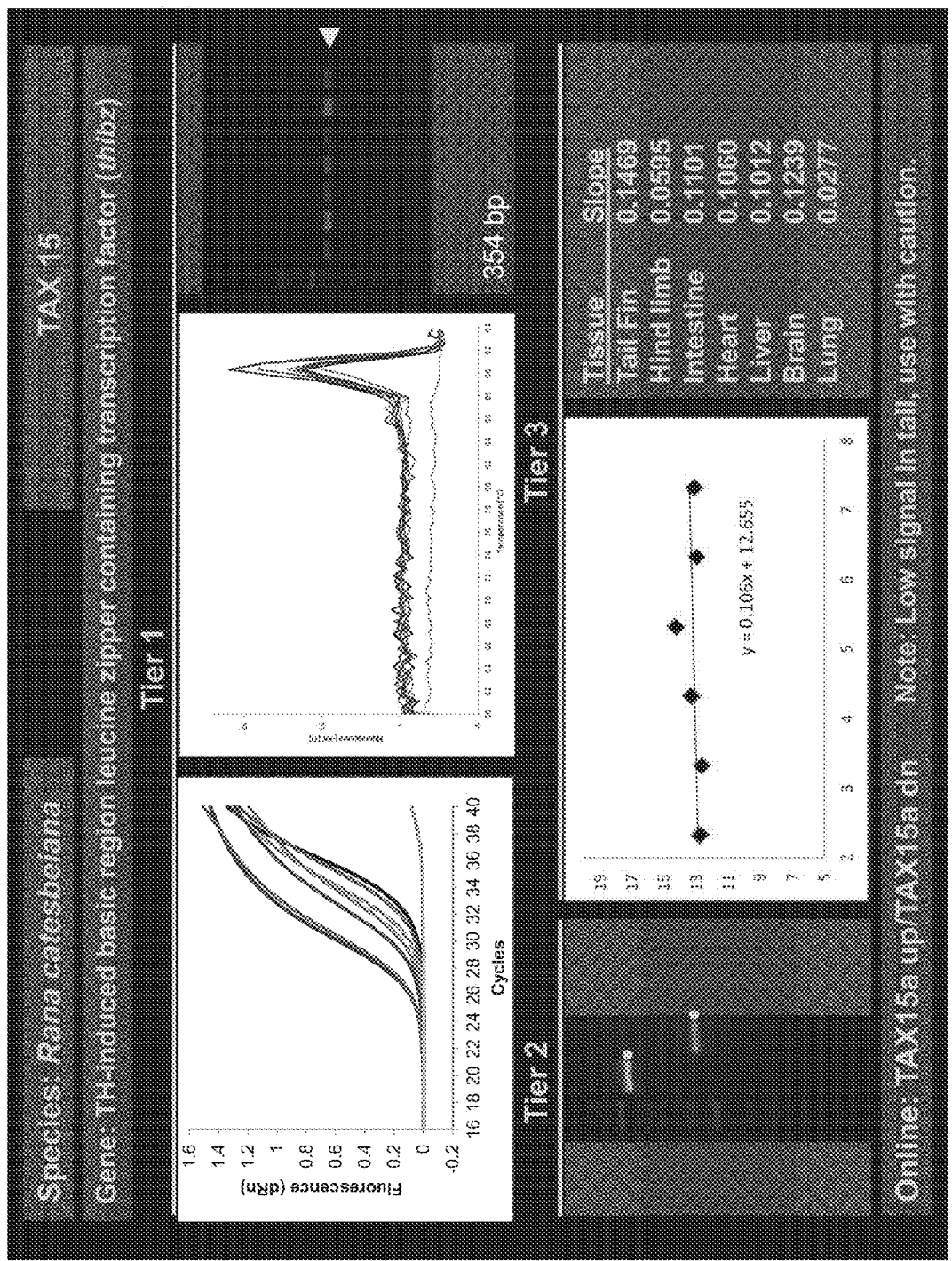
FIG. 2B(5)

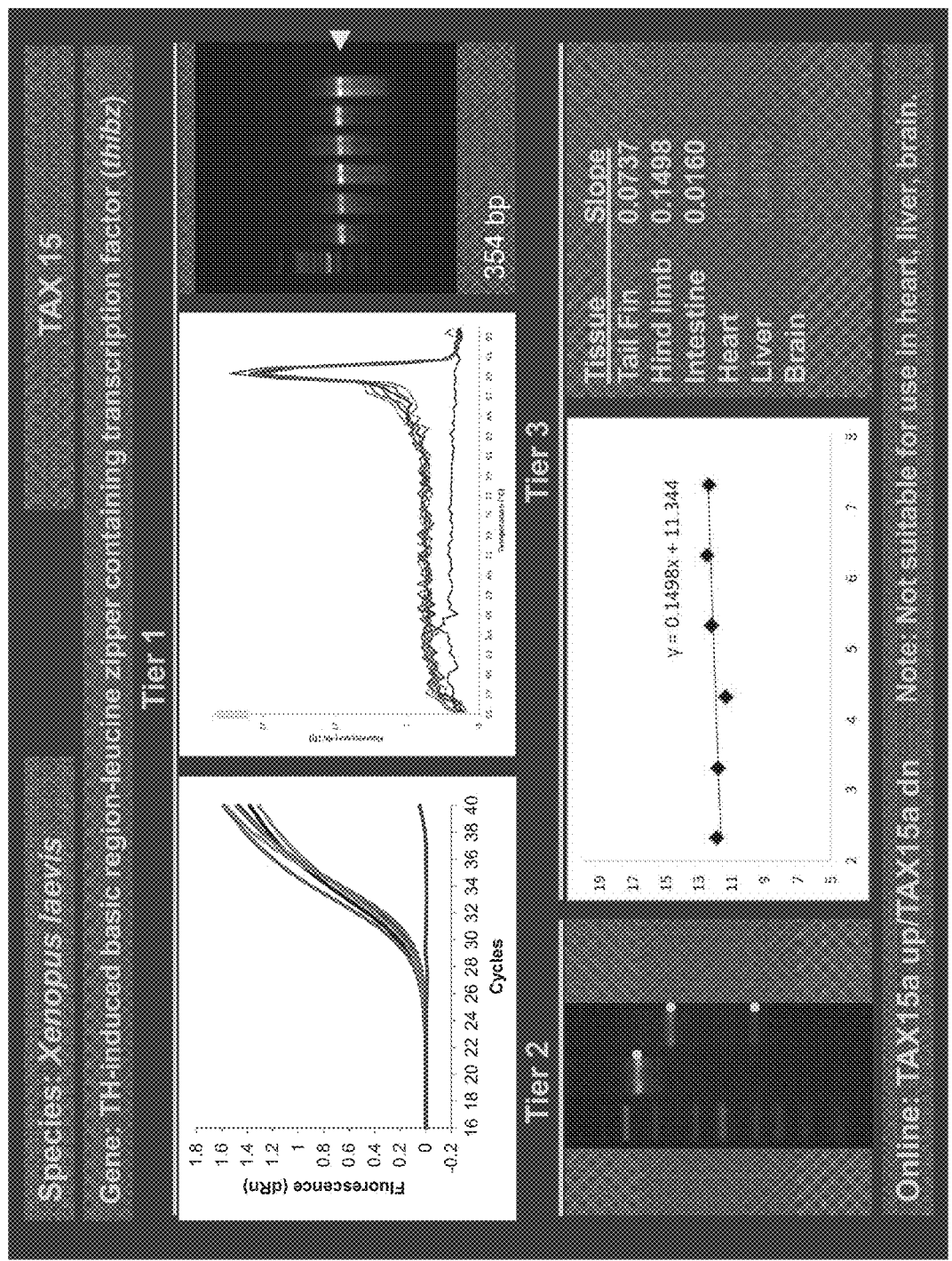
FIG. 2B(6)

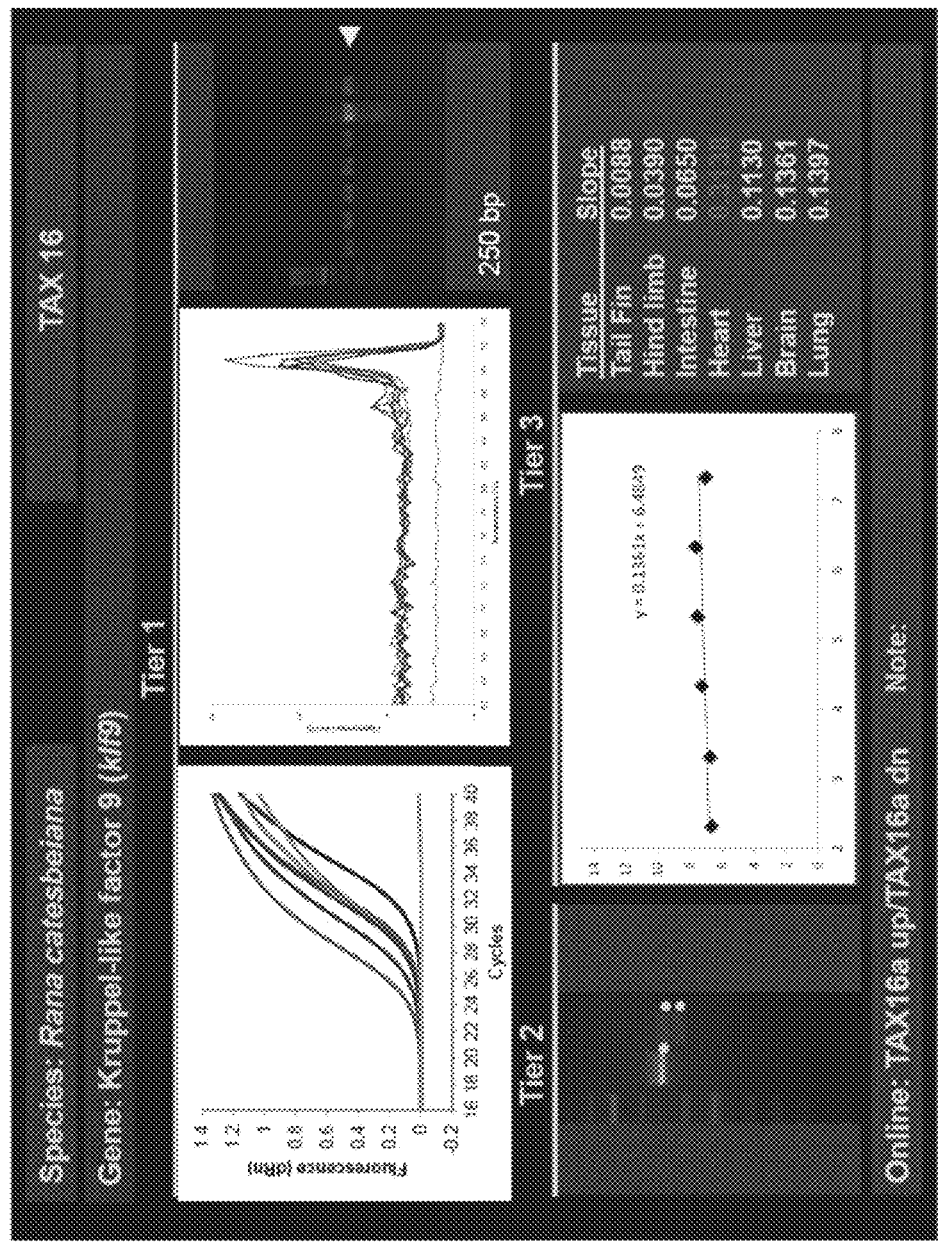
FIG. 2B(7)

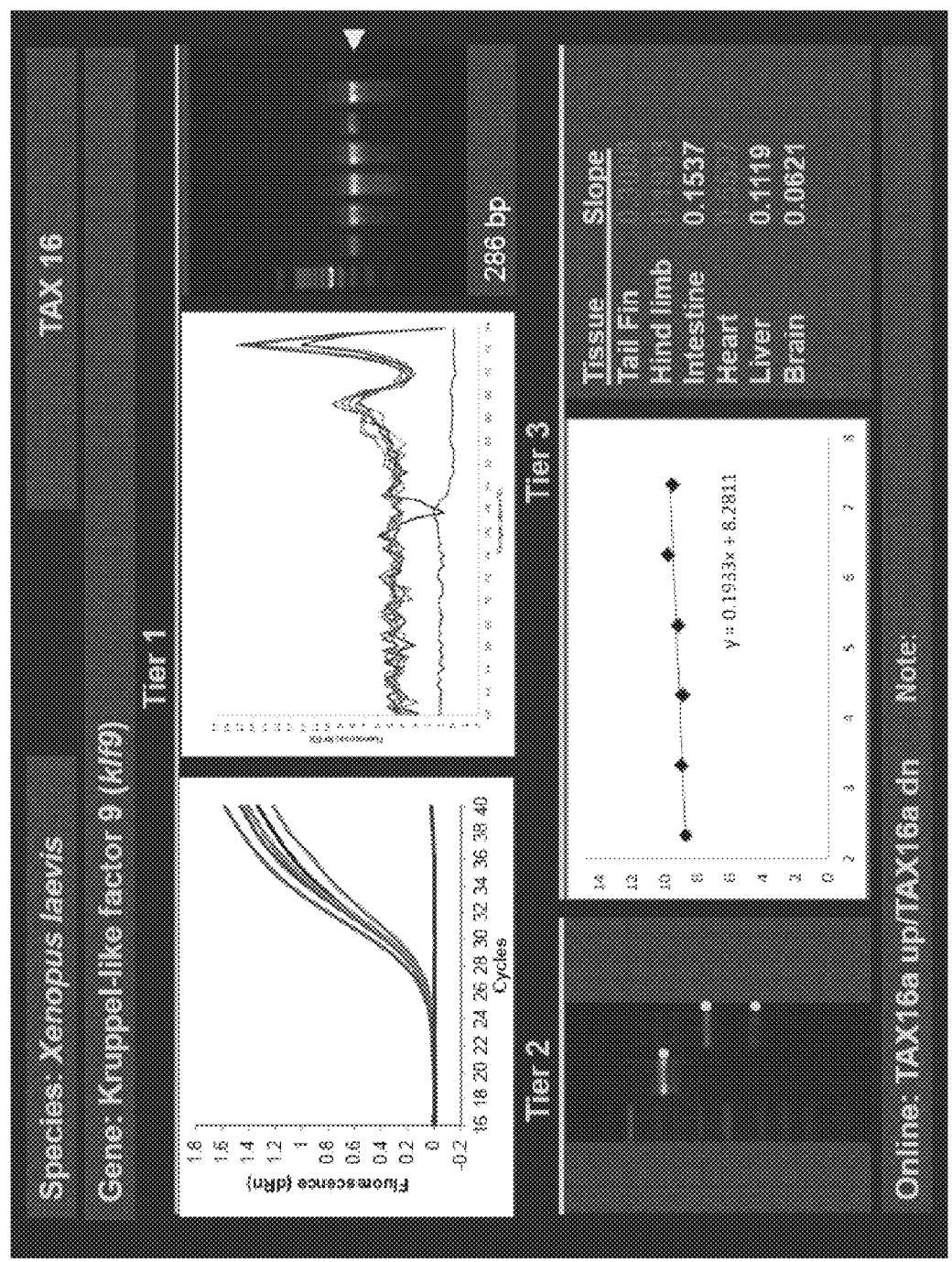
FIG. 2B(8)

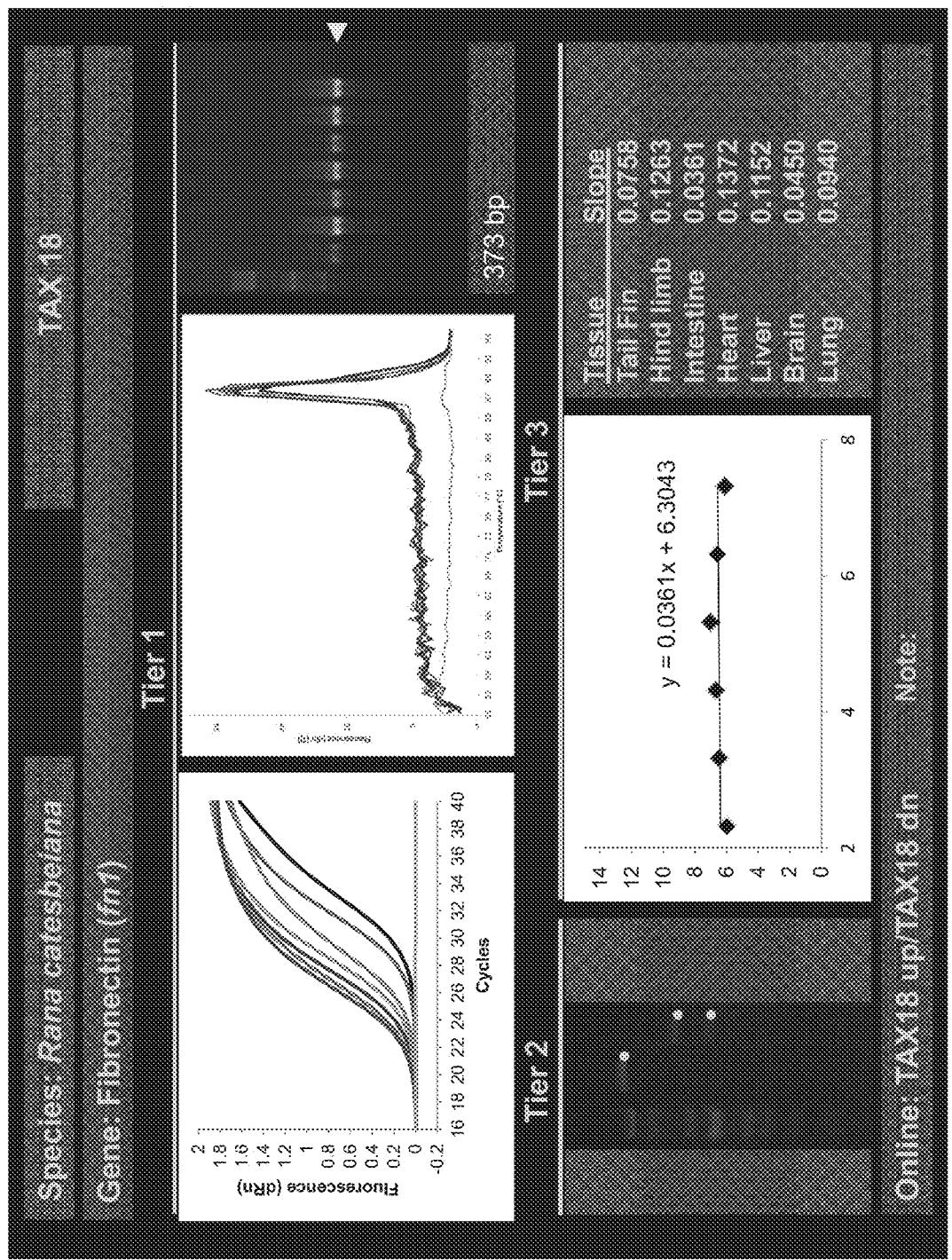
FIG. 2B(9)

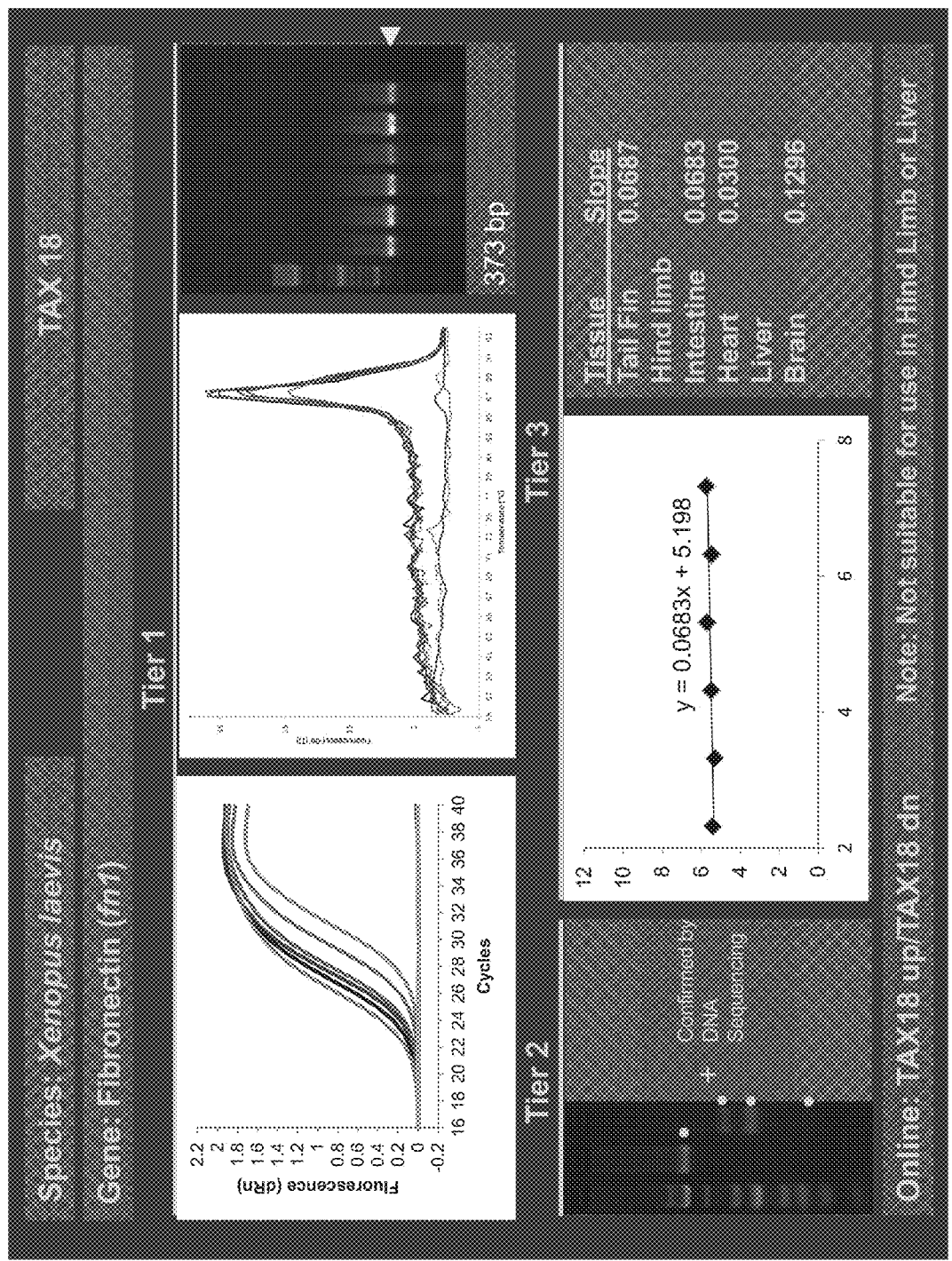
FIG. 2B(10)

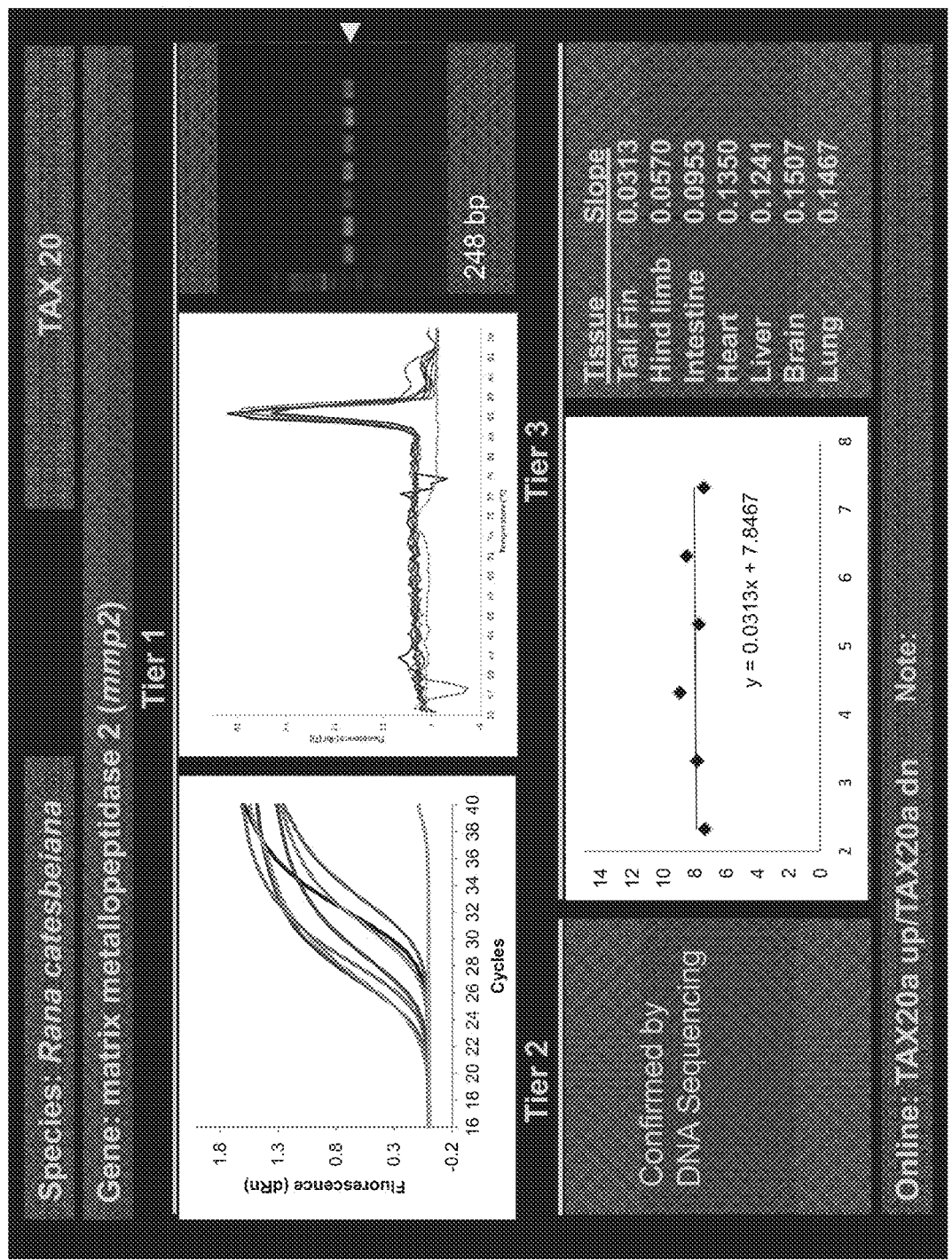
FIG. 2C(1)

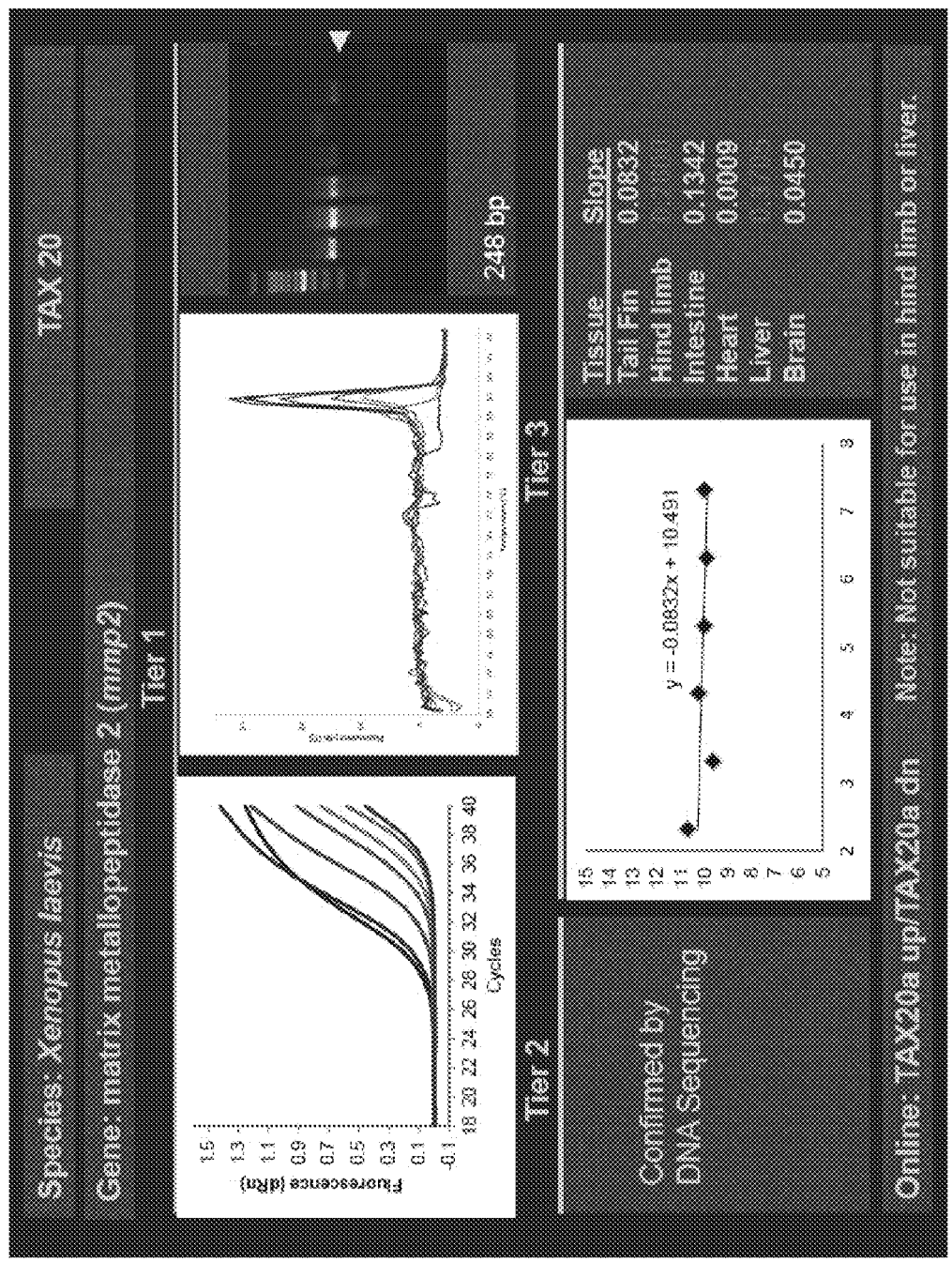
FIG. 2C(2)

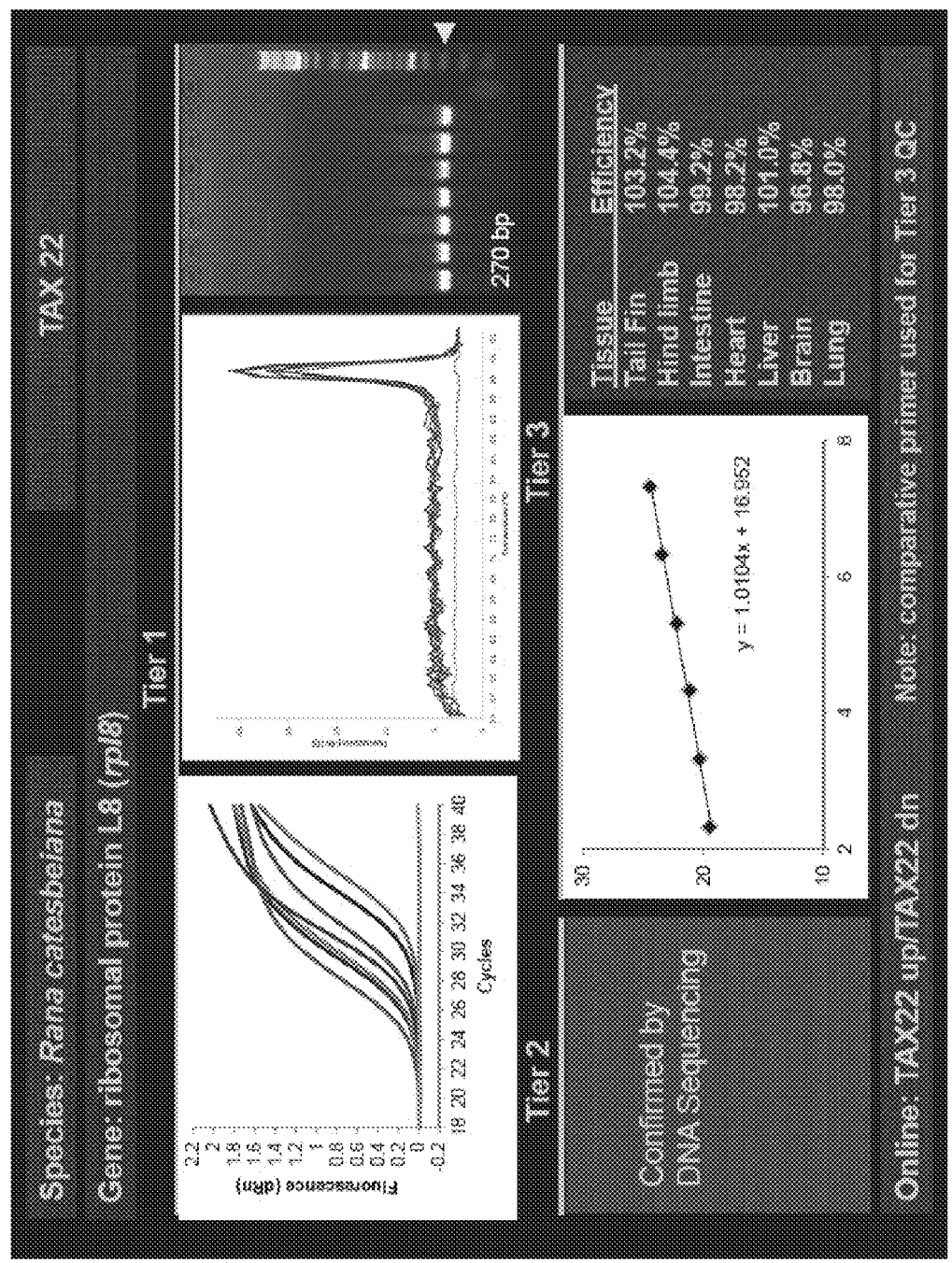
FIG. 2C(3)

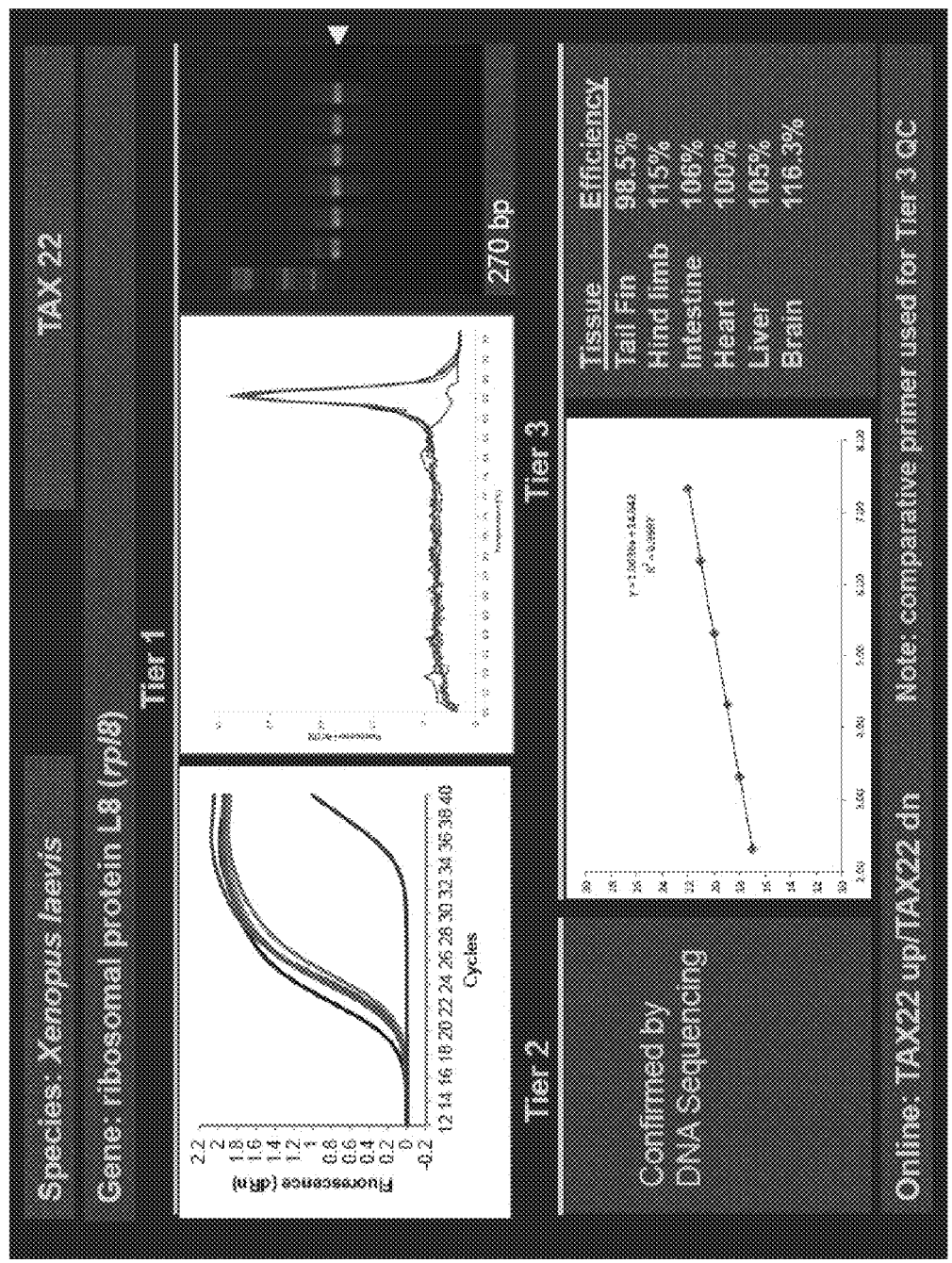
FIG. 2C(4)

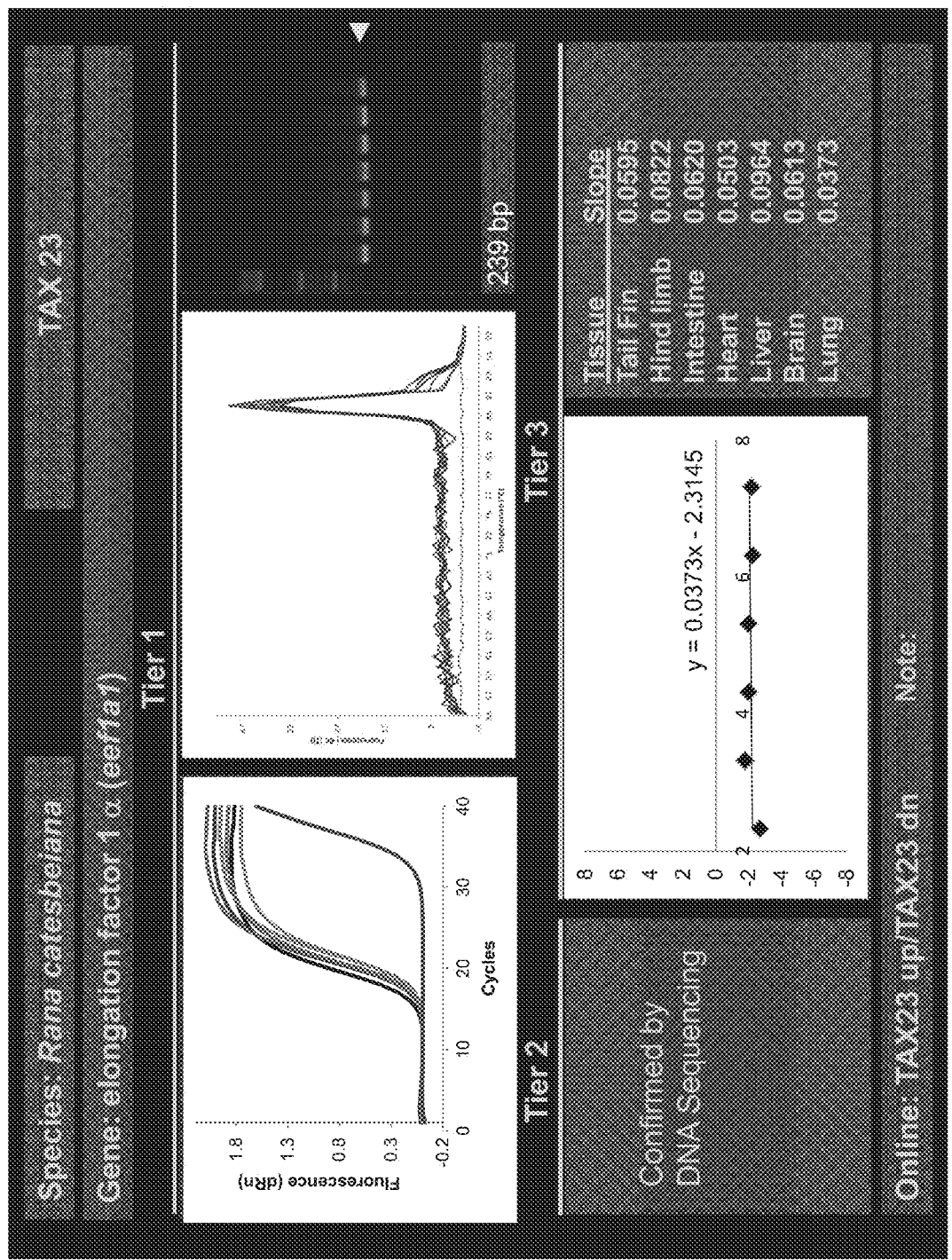
FIG. 2C(5)

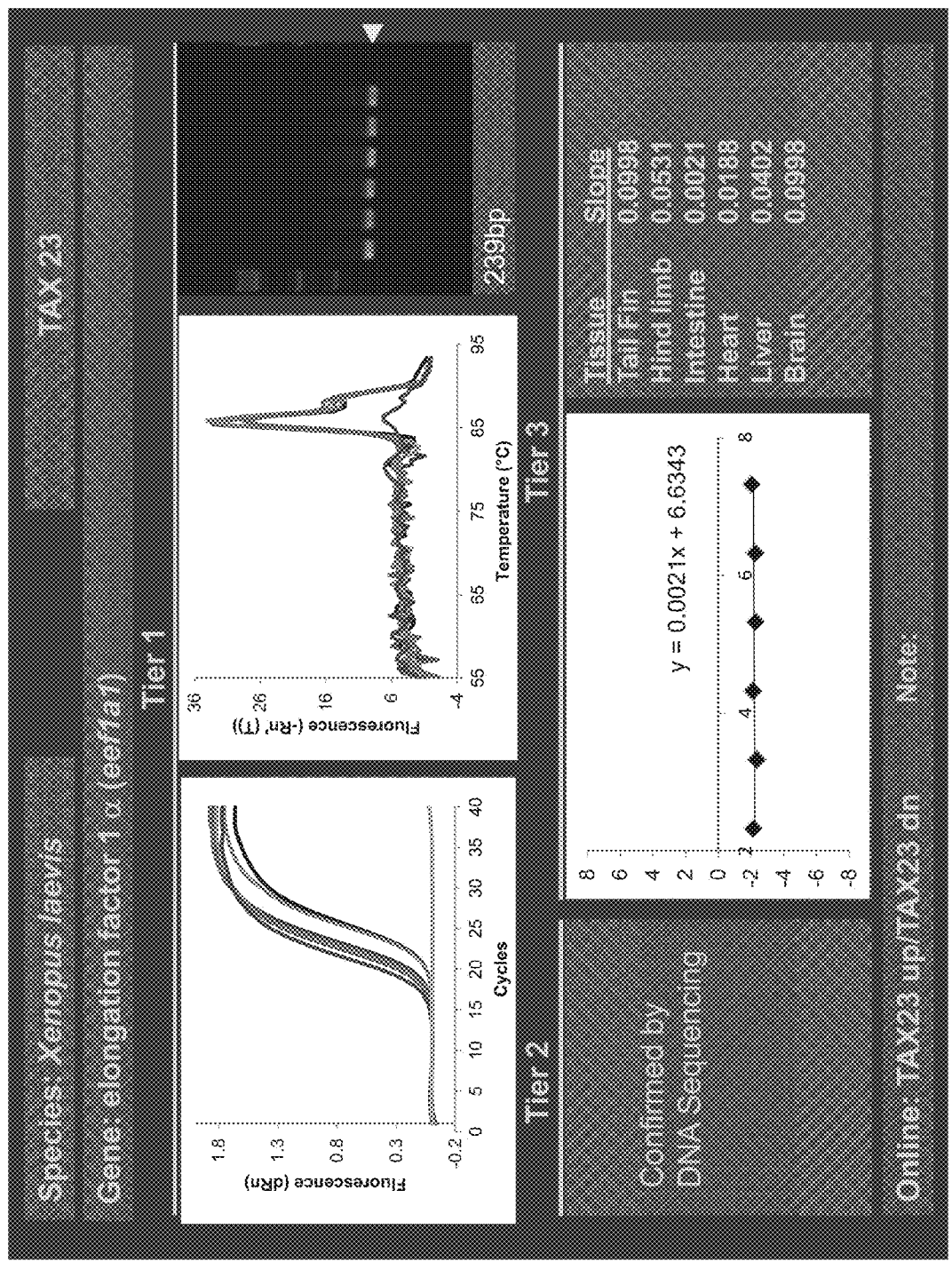
FIG. 2C(6)

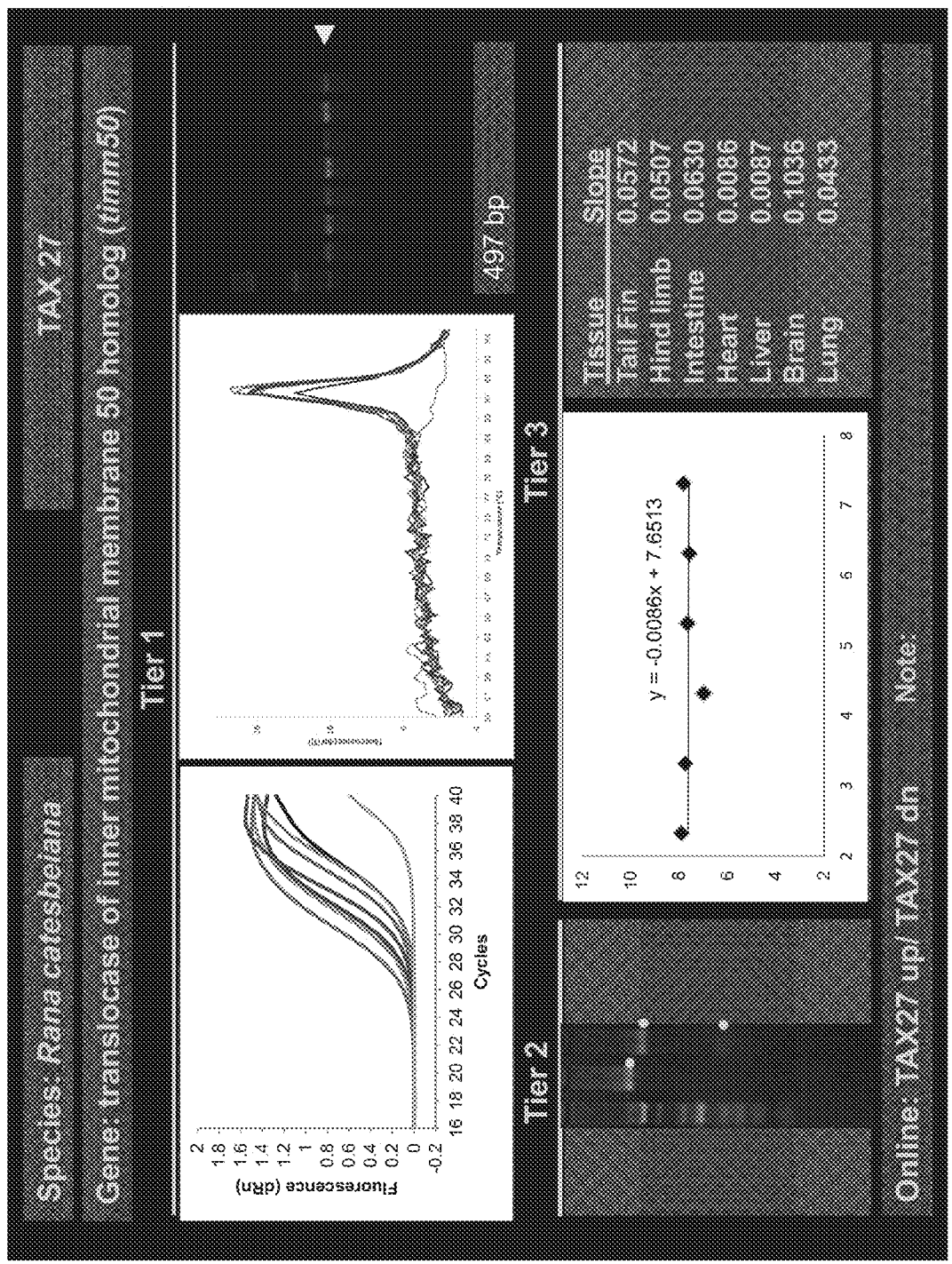
FIG. 2C(7)

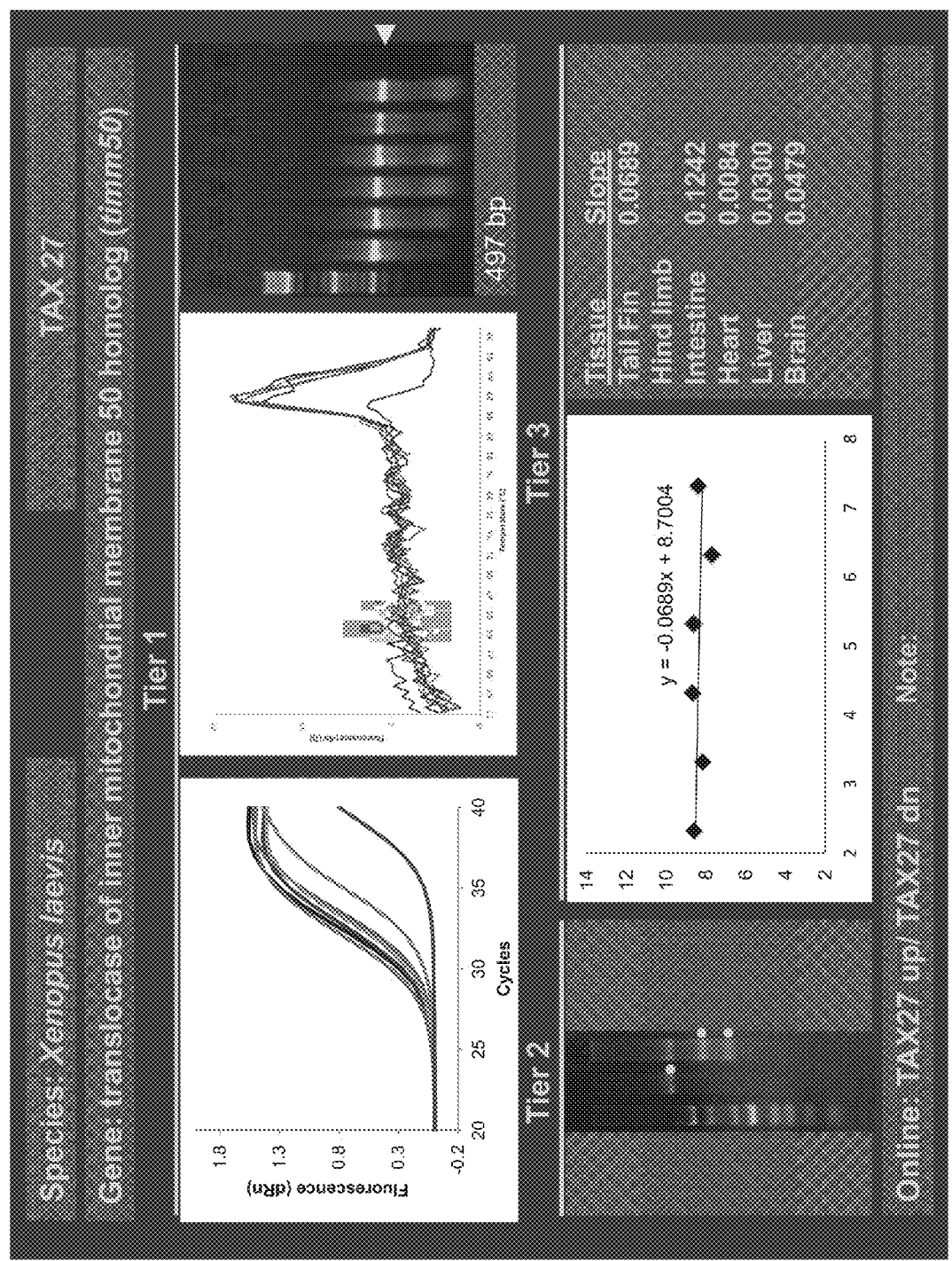
FIG. 2C(8)

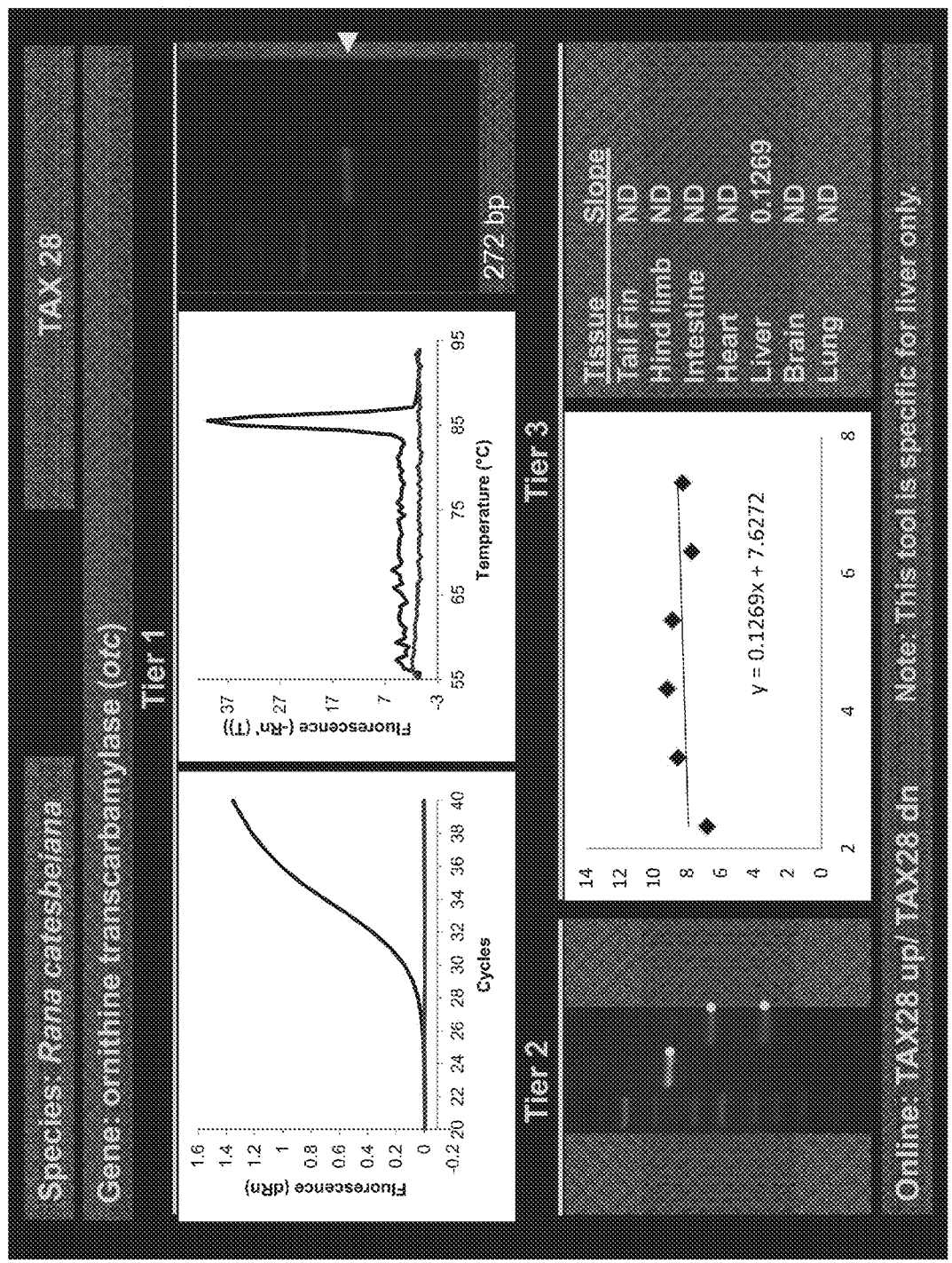
FIG. 2C(9)

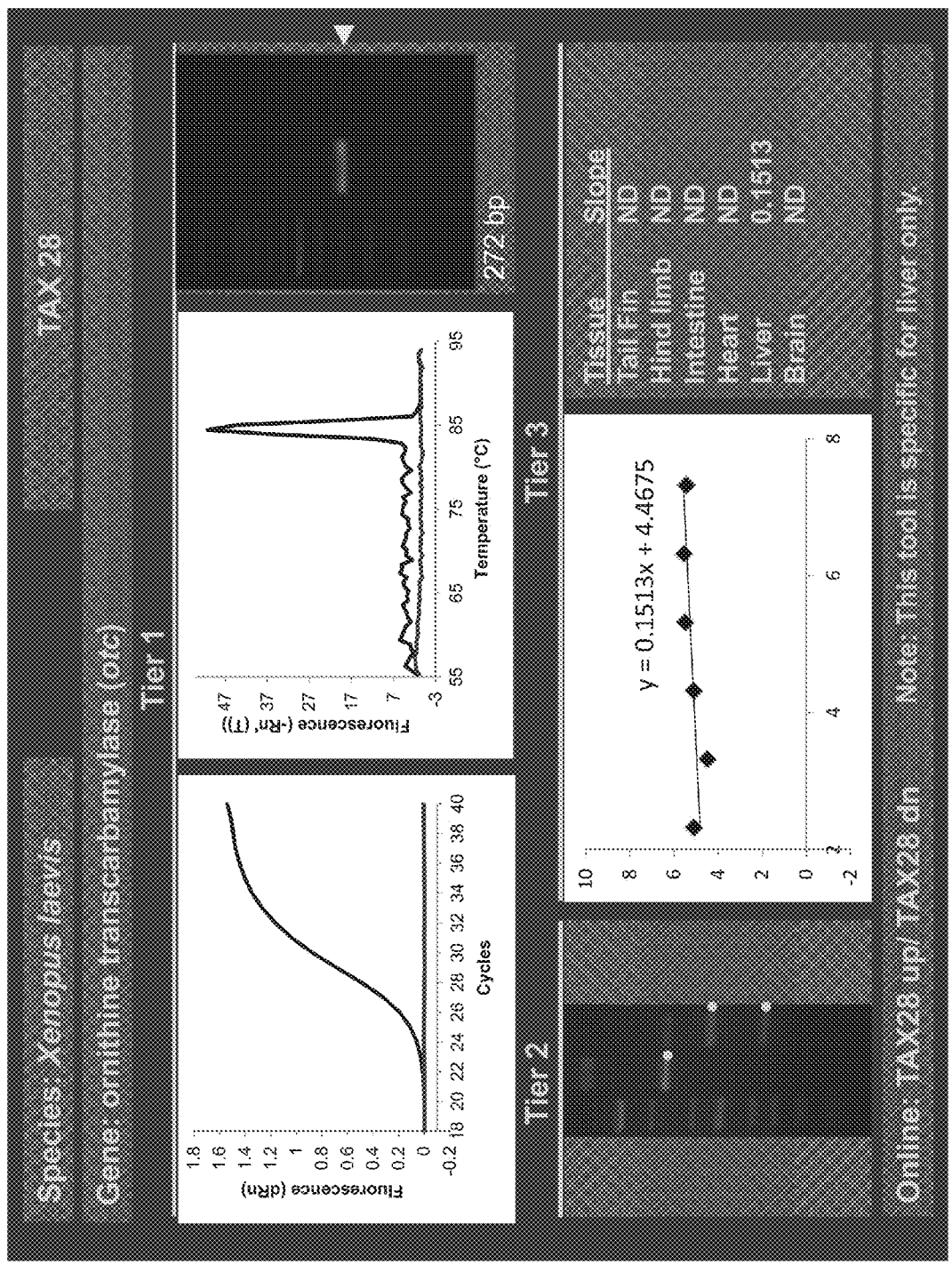
FIG. 2C(10)

ANURAN CROSS-SPECIES MOLECULAR SENSORS

CROSS REFERENCE TO RELATED APPLICATIONS

This application is a divisional of U.S. patent application Ser. No. 14/507,832, filed on Oct. 7, 2014, which claims the benefit of U.S. Provisional Patent Application No. 61/883,138, filed on Sep. 26, 2013, the entire contents of all of which are incorporated by reference.

FIELD OF THE INVENTION

The invention relates to biological assays and the study of animal development, environmental toxicology and ecological assessments.

SUMMARY OF THE INVENTION

The invention describes the DNA primer sequences designed for the determination of gene or transcript information from Anuran species. There are thousands of Anuran species known worldwide and obtaining genetic information from each species for the development of quantitative real time polymerase chain reaction (qPCR) assays is not feasible. Our invention is comprised of one or more specially-designed primer pairs that can be applied to diverse Anuran species spanning over hundreds of million years in evolution, including those species commonly used in laboratory studies for development and/or toxicity testing and sentinel species used for environmental toxicology or ecological assessment. Described herein are optimized conditions for use of these primers in examples of Anuran tissues. Another aspect of the invention is a rapid, sensitive, high-throughput assay useful for supporting potential risk assessment across vertebrate clades, and that is also useful for evaluation of complex contaminant mixtures.

BACKGROUND

Amphibians are used extensively as scientific model organisms, in health and environmental research, as test organisms, and have an undeniable role as sentinel species, as a food source, and in insect control. In contrast to mammals with extensive genomic resources, a particular challenge exists for evaluating gene expression endpoints in amphibian species where clades exhibit evolutionary divergence of over 300 million years (AmphibiaWeb 2012). Of the amphibians, the Anura-representing frogs and toads are the most numerous on the planet representing over 6,000 of the ~7,000 known species (AmphibiaWeb 2012). Despite this impressive number, only two closely-related Pipid species, *Xenopus laevis* and *Xenopus tropicalis*, have sufficient genomic resources for gene expression studies. Yet many other species including ones that have diverged over 200+ million years ago, serve as important species, regionally and globally. There is a lack of the most minimal genomic information leading to a significant investment in time and resources to even clone a portion of a single gene in order to develop validated gene expression tools for a species of interest. To circumvent this difficulty, we have developed a suite of qPCR-ready primer sets that identify particular genes and/or their transcripts. Each primer pair has been validated to function under stringent criteria in species as diverse as Pipids and Ranids. The use of these primer sets provides a simple, low-cost solution to the issue of cross-species comparison of responses and sensitivities.

Endocrine disruptors (EDCs) are chemicals, either environmental or man-made, that disturb the endocrine signaling pathways of humans and wildlife. EDC exposure often results in cancer, fertility problems, and other diseases (Vandenberg, Colborn et al. 2012). Therefore, the risk from these exposure effects has led to a great need for sensitive and appropriate methods for indicating deleterious EDC effects. For this reason, there is considerable interest in developing novel diagnostic assays to detect EDCs in the environment as well as in products meant for human consumption or that are used to package food products such as plastic food containers. Over 80,000 chemicals are registered for use in the US (NIEHS 2013) and there is increasing concern regarding their impact since it is now established that EDCs do not follow the classical rule of "the dose makes the poison" (Vandenberg, Colborn et al. 2012). Rather non-monotonic responses and low-dose effects are actually common in studies of natural hormones and EDCs and clear linkages between environmental exposures to EDCs and human diseases/disabilities are becoming evident (Vandenberg, Colborn et al. 2012). EDCs are generally found in low concentrations in the environment, but even minute quantities can have demonstrable impact as hormone disruptors. In fact biological activity can be detected below current analytical detection limits and measurement of EDCs in the context of complex mixtures such as municipal wastewater effluent is not necessarily a good predictor of biological activity (Quanrud and Propper 2010). Given that many aquatic ecosystems contain significant concentrations of environmental contaminants (Kolpin, Furlong et al. 2002), and that many of these compounds and/or their metabolites have been detected in human plasma (National Report on Human Exposure to Environmental Chemicals, Centers for Disease Control and Prevention, U.S. Department of Health and Human Services, http://www.cdc.gov/exposurereport), we have developed a suite of tools for indicating deleterious EDC effects. Such screens can be used as a first level evaluation of exposure health risk for both wildlife species and humans. Most of what we know about EDCs pertains to substances that disrupt estrogen signaling pathways and technologies to detect estrogenic EDCs have been developed (Van Aggelen, Ankley et al. 2010; Hecker and Hollert 2011).

BRIEF DESCRIPTION OF THE DRAWINGS

FIGS. 2A(1) through 2A(10); 2B(1) through 2B(10) and 2C(1)-2C(10) illustrate the results of the three-tiered quality assurance/control procedure demonstrating activity of the primer sets according to an embodiment of the invention.

DETAILED DESCRIPTION OF THE INVENTION

Figure 1:
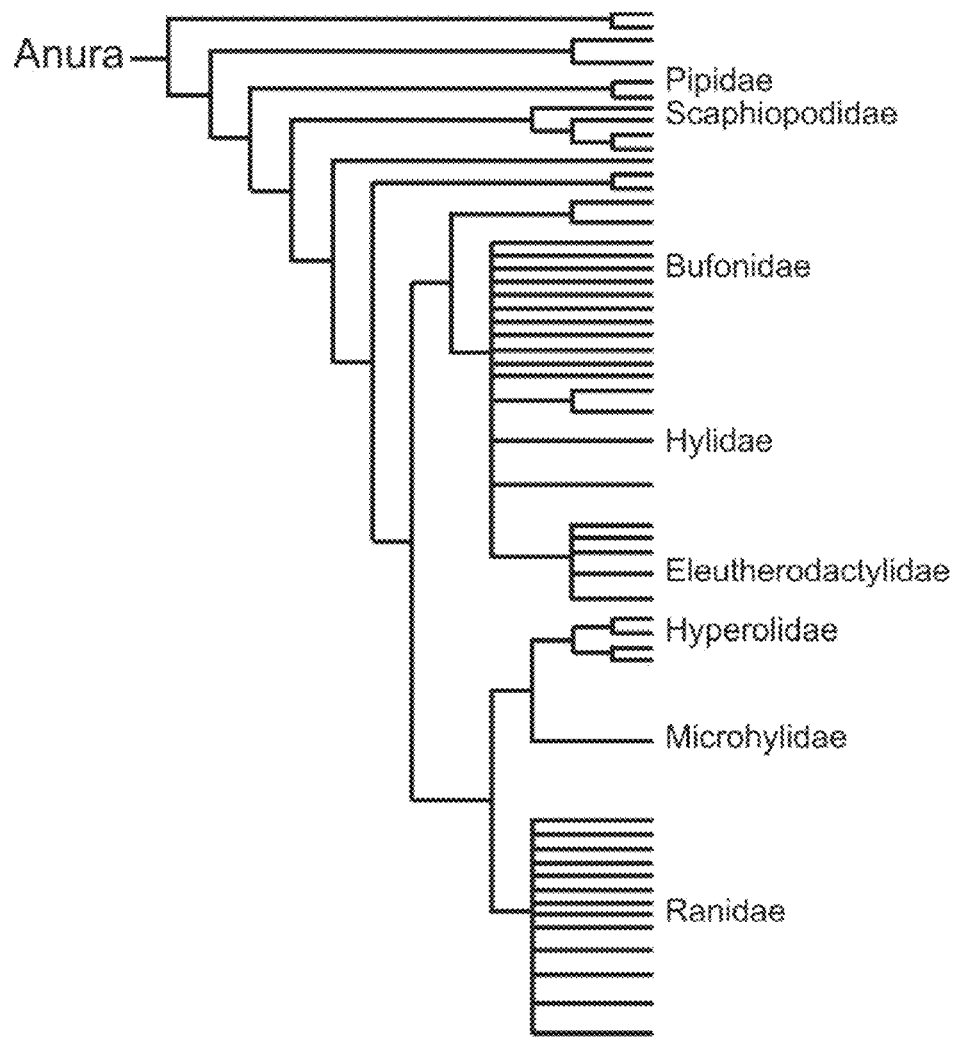
FIG. 1 is a cladogram depicting certain major families of the order Anura.

The thyroid hormones (THs) are crucial for normal growth, development, and metabolism in all vertebrates including humans (Morreale de Escobar, Obregon et al. 2004; Zoeller and Rovett 2004). In fetal and neonatal mammals, environmental contaminants such as perchlorate and polychlorinated biphenyls (PCBs) impact TH action contributing to serious defects in development and organ function including cognitive and motor deficits, abnormal bone growth, cardiac problems, and altered lipid metabolism (Zoeller and Rovett 2004; Bernal 2005; Cheng 2005; Siesser, Cheng et al. 2005; Liu and Brent 2010). The brain is particularly vulnerable (Porterfield 1994; Brucker-Davis 1998; Jones, Thoemke et al. 2005; Zoeller 2005; Zoeller and Crofton 2005) and the impact of mild hypothyroidism during critical developmental phases can have significant societal costs (Miller, Crofton et al. 2009). In amphibians, THs are required for tadpole metamorphosis into a juvenile frog and disruption of TH action results in the inability of the frog to develop normally (Shi 2000). Therefore, modification of TH action at early life history stages can lead to dramatic, deleterious outcomes for both humans and wildlife species. The mechanisms of TH action are common among vertebrates and involve a complex regulatory pathway yet the high degree of sensitivity to TH disruption of the tadpole has been identified as a powerful surrogate for the identification of chemicals and/or contaminants that perturb TH signaling in vertebrates (OECD 2009; Helbing 2012).

The invention presents an innovative method that relies upon a gene expression readout for detecting TH disrupting activities using Anuran species as model organisms, thereby greatly improving the power of the frog tadpole metamorphosis assay in predictivity and applicability to both laboratory testing and field applications across a range of all frog sentinel species. Moreover, the invention describes validated DNA primer sets for genes that are essential as references or "normalizers." These normalizers can be used alone or in conjunction with primers used to ascertain TH responsiveness increasing the breadth of utility and application. Furthermore, this set of normalizer genes is not just specific for thyroid function, but will also serve as a strong suite of reference genes for any type of qPCR application utilizing any response genes evaluated for any study using Anuran species.

The invention comprises one or more DNA primer pairs (Table 1) that have been designed against "normalizer" and/or responsive genes such that the same primer pair representing a given gene can reliably and quantitatively function in Anura regardless of species.

TABLE 1

Sequence, qPCR running conditions and characteristics of the Anuran DNA primer sets (Table 1 discloses SEQ ID NOS 1-30, respectively, in order of appearance)

| 999 Gene Code | Gene Targets | Gene Abbreviation | Primer UP | | Primer DOWN | | Annealing temperature | Thermocycle Profile | Amplicon |
|---|---|---|---|---|---|---|---|---|---|
| TAX1 | alpha 2 type 1 collagen | col1a2 | TAX1 up | CTGGTGGTG GATATGATG GT (SEQ ID NO. 1) | TAX1 dn | GAGTCTTAA GTCACGGCA AG (SEQ ID NO. 2) | 60 | 15s. 30s. 45s | 182 |
| TAX5 | cytoplasmic beta-actin | actb | TAX5 up | TACAGCTTC ACCACCACA G (SEQ ID NO. 3) | TAX5 dn | TCCACATCT GCTGGAAGG T (SEQ ID NO. 4) | 60/64* | 15s. 30s. 45s | 478 |
| TAX7 | ribosomal protein S10 | rps10 | TAX7 up | TTTGCYTGG CGKCACTTT T (SEQ ID NO. 5) | TAX7 dn | ARCRGCACT GCGYCTGTA (SEQ ID NO. 6) | 60 | 15s. 30s. 45s | 213 |
| TAX8 | myelin proteolipid protein A | plp1 | TAX8a up | TGGCTGARG GATTYTAYA CC (SEQ ID NO. 7) | TAX8 dn | ACAGCAGAG CAGGCAAMG A (SEQ ID NO. 8) | 60 | 15s. 30s. 45s | 256 |
| TAX9 | thyroid hormone receptor alpha | thra | TAX9 up | TGATAAGGC CACAGGRTA CCACTA (SEQ ID NO. 9) | TAX9 dn | CGGGTGATC TTGTCGATR A (SEQ ID NO. 10) | 60 | 15s. 30s. 45s | 141 |
| TAX10 | thyroid hormone receptor beta | thrb | Tax10 up | CTCATAGAA GAAAACAGA GAAAARAGA (SEQ ID NO. 11) | TAX10 dn | GAAGGCTTC TAAGTCCAC TTTTCC (SEQ ID NO. 12) | 60 | 15s. 30s. 45s | 237 |

TABLE 1-continued

Sequence, qPCR running conditions and characteristics of the Anuran DNA primer sets (Table 1 discloses SEQ ID NOS 1-30, respectively, in order of appearance)

| 999 Gene Code | Gene Targets | Gene Abbreviation | | Primer UP | | Primer DOWN | Annealing temperature | Thermocycle Profile | Amplicon |
|---|---|---|---|---|---|---|---|---|---|
| TAX12 | deiodinase type II | dio2 | Tax12a up | CCTGGCTCT STAYGACTC (SEQ ID NO. 13) | TAX12d dn | RGCTGATCC RAARTTGAC (SEQ ID NO. 14) | 62 | 15s. 30s. 45s | 295 |
| TAX15 | TH-induced basic region leucine zipper containing transcription factor | thibz | TAX15a up | ASCTCCRCA GAAYCAGCA (SEQ ID NO. 15) | TAX15a dn | TCACGTACC AGGCCAAAA (SEQ ID NO. 16) | 62 | 15s. 30s. 30s | 354 |
| TAX16 | Kruppel-like factor 9 | klf9 | TAX16a up | CYGCTCAGT GTCTGGTGT (SEQ ID NO. 17) | TAX16a dn | ARGGGCCGG TACTTGTTT (SEQ ID NO. 18) | 62 | 15s. 30s. 30s | 250 |
| TAX18 | fibronectin | fn1 | Tax18 up | GTTGCCATG ARGGWGGAC (SEQ ID NO. 19) | TAX18 dn | CCATTGCCW GTGCAGATA (SEQ ID NO. 20) | 60 | 15s. 30s. 45s | 373 |
| TAX20 | matrix metallopeptidase 2 | mmp2 | TAX20a up | TACAACAGC TGCACTGAT (SEQ ID NO. 21) | TAX20a dn | TCCTTGTCA TAGTCTTCT GT (SEQ ID NO. 22) | 62 | 15s. 30s. 30s | 248 |
| TAX22 | ribosomal protein L8 | rpl8 | TAX22 up | CAGGGGACA GAGAAAAGG TG (SEQ ID NO. 23) | TAX22 dn | TGAGCTTTC TTGCCACAG (SEQ ID NO. 24) | 60 | 15s. 30s. 45s | 270 |
| TAX23 | elongation factor 1 alpha | eef1a1 | TAX23 up | GCTGCTGGT GTTGGTGAR T (SEQ ID NO. 25) | TAX23 dn | AGCATGTTG TCACCRTTC C (SEQ ID NO. 26) | 60 | 15s. 30s. 45s | 257 |
| TAX27 | translocase of inner mitochondrial membrane 50 homolog | timm50 | TAX27 up | GCTWCAYCC AGAGTGGTC GTT (SEQ ID NO. 27) | TAX27 dn | GCTGYTCCT CCTGCTCCA (SEQ ID NO. 28) | 60 | 15s. 30s. 45s | 497 |
| TAX28 | ornithine transcarbamylase | otc | TAX28 up | YATGACYGA TGCTGTTCT AG (SEQ ID NO. 29) | TAX28 dn | CATAWCCCT TTGGTGTTG C (SEQ ID NO. 30) | 60 | 15s. 30s. 30s | 272 |

*Xenopus laevis/Rana catesbeiana annealing temperatures

Examples of the use of the invention are to indicate responsiveness to thyroid hormone action or indicators of developmental phases attained. We demonstrate that these primers function well across the evolutionary range of Anurans and also demonstrate the range of tissues in which the primers may be reliably used in the context of assessing mRNA (cDNA) levels or gene levels (genomic DNA). Finally, we also present a specific application of the technology to identifying perturbations in thyroid hormone signaling.

A great diversity of Anuran species are used in a broad range of disciplines such as developmental and cancer biology, physiology, ecology, molecular biology, biochemistry, from egg to adult stages. Every qPCR-based study requires the use of reference gene transcripts or genes in order to be able to interpret experimental data. The basic assumption is that the reference gene(s) do not vary due to the treatment condition of the experiment and the type of reference or "normalizer" varies depending upon experimental context (Bustin, Beaulieu et al. 2010). Therefore, a selection of normalizer gene candidates is necessary as well as the identification and use of multiple normalizers to enhance the robustness of the data set. Furthermore, this set of normalizer genes is not just specific for thyroid function, but will also serve as a strong suite of reference genes for any type of qPCR application utilizing any response genes evaluated for any study using Anuran species.

The inventors have identified TH-responsive gene candidates that are common between mammals and frogs that would serve to act as meaningful indicators of TH disruption within the context of an amphibian metamorphosis assay (AMA) (Searcy, Beckstrom-Sternberg et al. 2012). The suggested species for the AMA is *Xenopus laevis* with additional interest in using the related Silurana (*Xenopus*) *tropicalis* (Mitsui, Fujii et al. 2006). However, several nations are also interested in using native species relevant to their environments such as *Rana pipiens* and Pseudacris regilla (Canada), *Rana temporaria* (Europe), and *Rana rugosa* (Japan), *Rhinella* (*Bufo*) *marinus* (Latin America, Australia and SE Asia), or the only truly cosmopolitan frog, *Rana catesbeiana* (Bruno 2001; Veldhoen, Skirrow et al. 2006; Oka, Miyahara et al. 2009; Marlatt, Veldhoen et al. 2013). Toxicological evaluations on a variety of species is highly desirable to enable direct comparison between species for sensitivities and evaluation of the impact of different life histories and genome compositions (Relyea and Jones 2009; Helbing 2012).

The designed primers were subjected to tests of qPCR specificity and suitability within each tissue of interest in BOTH *Xenopus laevis* and *Rana catesbeiana*. These two species bracket the most commonly used frog families spanning ~200 million years of evolution (Sumida, Kato et al. 2004) (FIG. 1). The inventors determined that if the primer pairs work well for both species, then the likelihood that they work for intermediate species is assured.

FIG. 1 is an anuran cladogram depicting major families of current interest in the scientific and conservation realm. *Xenopus laevis* is a member of the Pipidae whereas *Rana catesbeiana* is a member of the Ranidae. Adapted from AmphibiaWeb: Phylogenetic view of *Amphibia* [web application] 2012. UC Regents, Berkely, Calif., available: http:amphibiaweb.org (14 May 2012).

The inventors' rigorous design and verification protocol includes amplicon sequence confirmation, routine melting curve analysis, generation of standard curves for each primer set, and determination of amplification efficiency. All procedures are compliant with the Minimum Information for Publication of qPCR Experiments (MIQE précis) guidelines (Bustin, Beaulieu et al. 2010). qPCR technology presents the most accurate and sensitive genetic technique available that enables high-throughput detection of low abundance mRNA transcripts. Due to its relative robustness and low operating cost, this technology is currently the most conducive to the demands of the regulatory context and the assays developed have immediate translation to regulatory labs. We elected to focus on a SYBR-based detection method because this is the presently least expensive to run (good for the price point of the end user) and more labs have access to the equipment necessary for readout therefore increasing the market potential.

Our primer quality assurance/control procedure has been standardized and follows a three-tiered quality control and quality assurance (QC/QA) process, as follows.

Tier 1 QC/QA

Total RNA from the target animal species and tissue type is converted to complementary DNA (cDNA) and queried with the putative qPCR primer pairs designed against genes of interest. The function of each primer pair in the qPCR assay is assessed for amplification signal representative of a single targeted cDNA product. Control qPCR reactions containing no cDNA are performed to evaluate background inter- and intra-primer interactions that can contribute to signal noise. Thermocycle conditions are chosen for each gene-specific primer pair that maximizes signal specificity while minimizing background noise. The DNA products generated in the qPCR assay are subsequently confirmed to be the correct predicted length through agarose gel electrophoretic analysis.

Tier 2 QC/QA

The specificity in DNA amplification of each qPCR primer pair is further confirmed through isolation and sequence-dependent assessment of qPCR-generated DNA products that contribute to the SYBR-based signal. Two methods can be used: 1) mapping of restriction endonuclease-derived fragments of qPCR amplified DNA, or 2) DNA sequencing of the product of qPCR. This serves to confirm the specificity of the qPCR SYBR-signal collected and the identity of the gene sequence amplified by each primer pair used in qPCR.

Tier 3 QC/QA

To ensure that the SYBR-based signal data collected during qPCR can be employed in a quantitative manner, similarity in relative primer pair performance must be satisfied using information obtained through qPCR analysis of a dilution series of target cDNA from the tissue of interest. The sensitivity and ability of each gene-specific primer pair to detect linear changes in target cDNA abundance is assessed. Primer pair performance of a test gene is compared to the performance of primer pairs from reference genes to ensure comparable amplification efficiencies. Tissue context is important because we and others have found that some primers, although specific for their gene target, can display reduced performance in certain tissue contexts.

Figure 8:
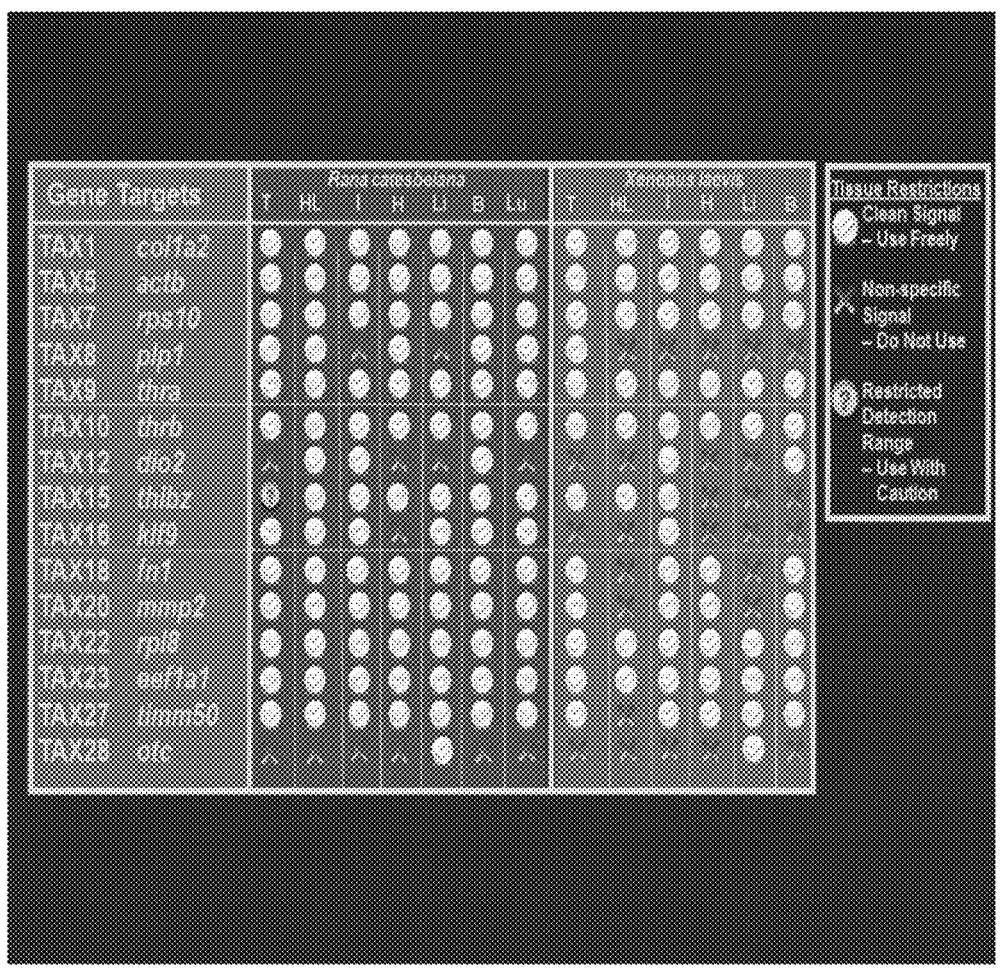
FIG. 8 is a summary of tissue types in which each primer set is usable in *Rana catesbeiana* and *Xenopus laevis*.

The results of the three tier QC/QA process for each of the primer sets listed in Table 1 are presented in FIG. 2. This demonstrates that the primer sets work to specifically amplify the appropriate amplicon in a variety of contexts. A summary of which tissue types are usable for transcriptomics analyses for each primer set is found in FIG. 8. In FIG. 8, the particular tissues of *Rana catesbeiana* and *Xenopus laevis* in which each primer set is usable are denoted as follows:

T=tail fin
HL=hind limb
I=intestine
H=heart
Li=liver
B=brain
Lu=lung

The QC/QA results plus evidence of functionality in *Rana catesbeiana* and *Xenopus laevis* tissues are presented in FIG. 2, which is comprised of FIGS. 2A(1) through FIGS. 2A(10); FIGS. 2B(1) through FIGS. 2B(10) and FIGS. 2C(1) through FIGS. 2C(10). In these figures, results of the three tier QC/QA process by primer set on tissues from *Rana catesbeiana* and *Xenopus laevis* are shown. Each of the 30 primer sets is identified at the top of each drawing figure. Quality assurance (QA) of each primer pair is established through a three-tier evaluation procedure that includes:

Tier 1, a clean cDNA-dependent signal return with low background noise determined through amplification that is associated with the production of a single DNA product for each anuran tissue type as determined through dissociation curves and electrophoretic analyses;

Tier 2, sequence-dependent confirmation of gene-specific targeting through restriction endonuclease mapping or direct DNA sequencing of the isolated amplified DNA product; and Tier 3, primer pair comparative efficiency assessment across a tissue-specific cDNA dilution series as it related to the qPCR performance of the selected reference primer pair on the same cDNA dilution series. The slope of the interrelated qPCR performance must be ≤0.1 to be considered suitable for that tissue type.

The decision of whether a primer pair would be used to discern a gene transcript as a normalizer or test is highly dependent upon the experimental context and includes considerations of tissue-type, sample time, exposure type, and species examined.

Examples of normalizer gene candidates that would be used in any qPCR experiment to act as input reference include, but are not limited to: col1a2, actb, fn1, rps10, plp1, rpl8, eef1a1 and timm50 (Table 1).

Examples of thyroid hormone-responsive gene candidates in *Rana catesbeiana* (FIGS. 3 and 4) and *Xenopus laevis* (FIG. 5) include, but are not limited to: col1a2, actb, plp1, thra, thrb, dio2, thibz, klf9, fn1, mmp2, and otc.

Figure 3:
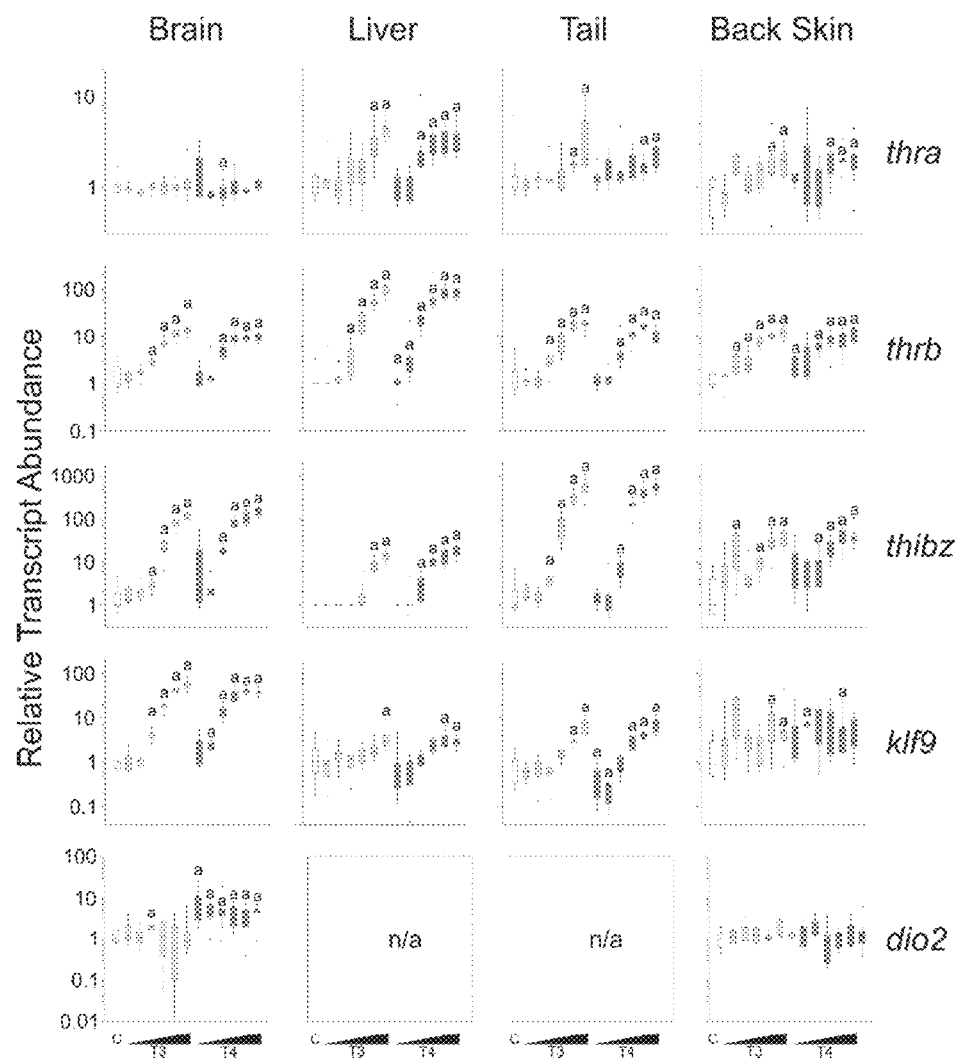
FIG. 3 illustrates the results of a demonstration of thyroid hormone responsiveness of the target gene transcripts in *Rana catesbeiana* according to an embodiment of the invention.

FIG. 3 illustrates a demonstration of thyroid hormone responsiveness of the target gene transcripts in *Rana catesbeiana*. Fold-change expression data for the indicated gene transcripts as determined using the comparative Ct method (ΔΔCt) using multiple gene transcript normalizers. Data are expressed in box plots as fold-change in expression levels relative to the vehicle control group. Premetamorphic tadpoles were injected with either vehicle control (C) or the indicated concentration of thyroid hormone and the tissues collected after 48 hours. The concentration for $T_3$ exposures are 0.01, 0.1, 1.0, 10, 25, and 50 nM and 0.05, 0.5, 5.0, 50, 125, and 250 nm for $T_4$. The medians are shown as solid black lines within the box and the box indicates the $25^{th}$ and $75^{th}$ percentiles. Whiskers indicated the range. "a": significantly different from the vehicle control group (p<0.05). "n/a" means not expressed in that tissue.

Figure 4:
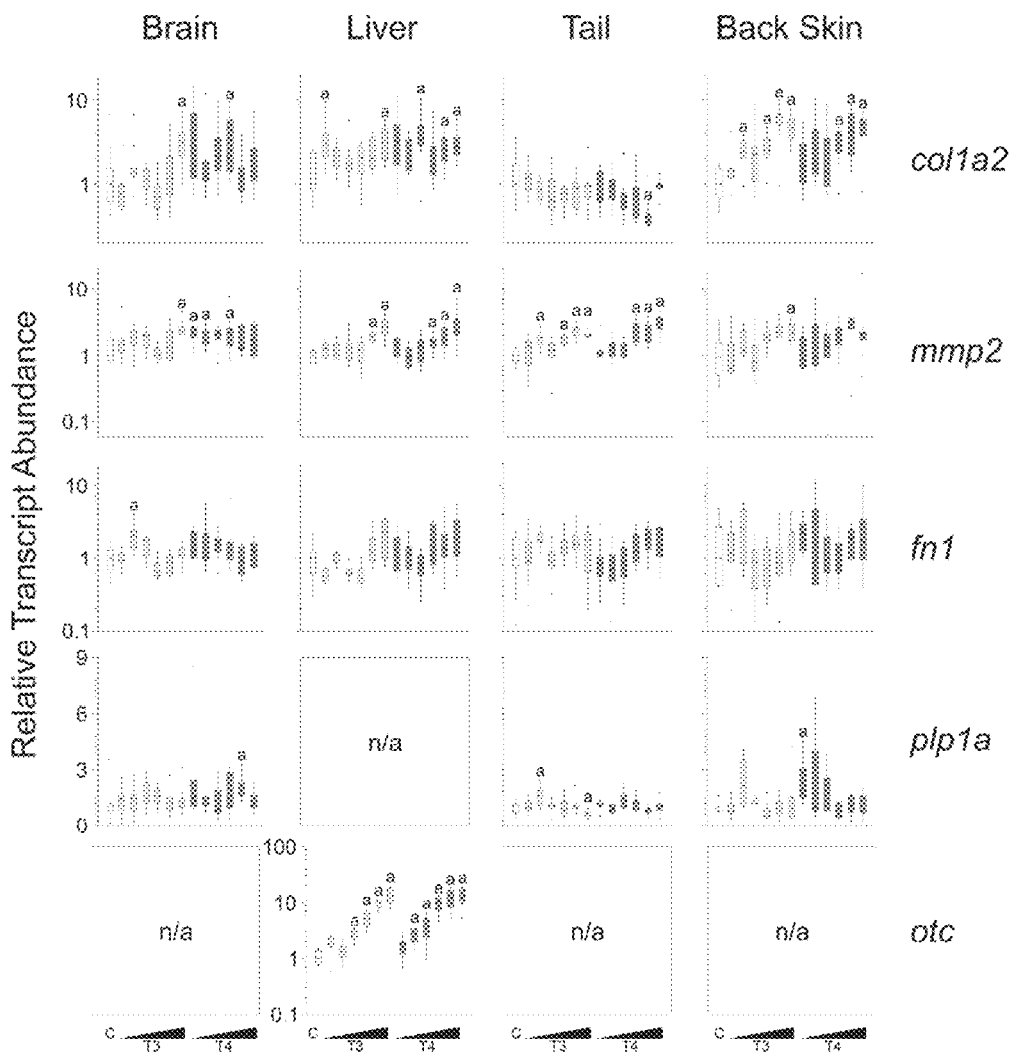
FIG. 4 is another illustration of the results of a demonstration of thyroid hormone responsiveness of the target gene transcripts in *Rana catesbeiana* according to an embodiment of the invention.

FIG. 4 illustrates a demonstration of thyroid hormone responsiveness of the target gene transcripts in *Rana catesbeiana*. Fold-change expression data for the indicated gene transcripts as determined using the comparative Ct method (ΔΔCt) using multiple gene transcript normalizers. Data are expressed in box plots as fold-change in expression levels relative to the vehicle control group. Premetamorphic tadpoles were injected with either vehicle control (C) or the indicated concentration of thyroid hormone and the tissues collected after 48 hours. The concentration for $T_3$ exposures are 0.01, 0.1, 1.0, 10, 25, and 50 nM and 0.05, 0.5, 5.0, 50, 125, and 250 nm for $T_4$. The medians are shown as solid black lines within the box and the box indicates the $25^{th}$ and $75^{th}$ percentiles. Whiskers indicated the range. "a": significantly different from the vehicle control group (p<0.05). "n/a" means not expressed in that tissue.

Figure 5:
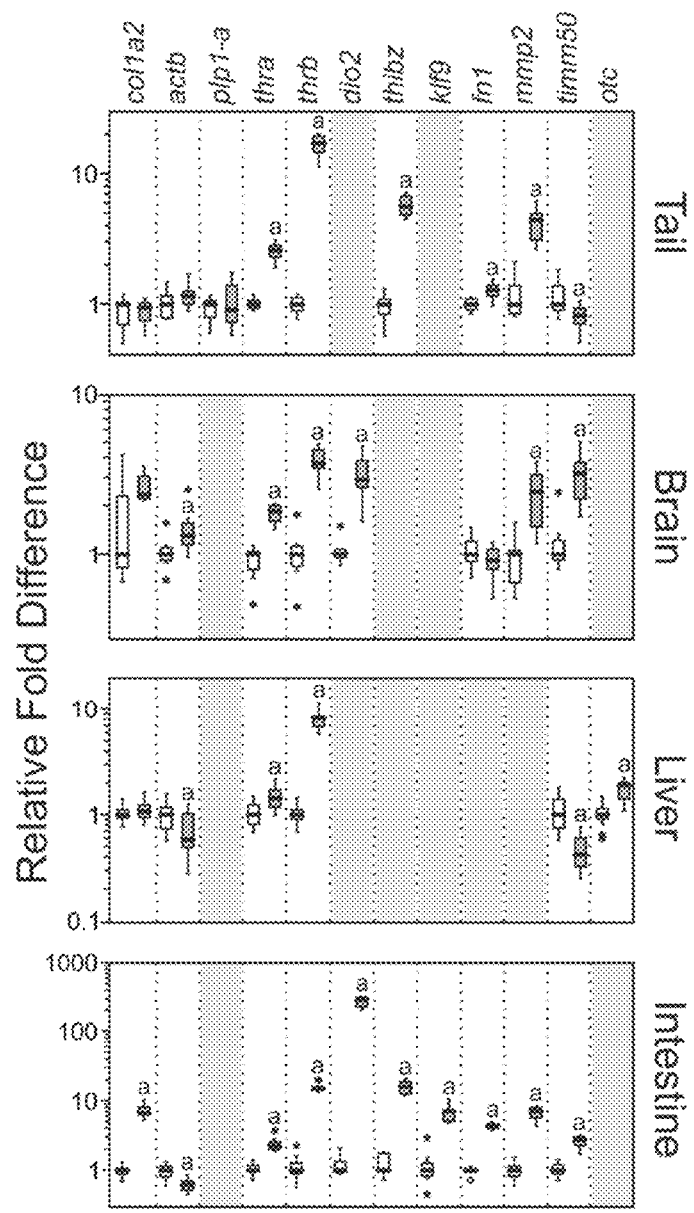
FIG. 5 is an illustration of the results of a demonstration of thyroid hormone responsiveness of the target gene transcripts in *Xenopus laevis* according to an embodiment of the invention.

FIG. 5 illustrates a demonstration of thyroid hormone responsiveness of the target gene transcripts in *Xenopus laevis* in the tail, brain, liver, and intestine. Fold-change expression data for the indicated gene transcripts as determined using the comparative Ct method (ΔΔCt) using multiple gene transcript normalizers. Data are expressed in box plots as fold-change in expression levels relative to the vehicle control group. Premetamorphic tadpoles were immersed in water containing vehicle control of 10 nM $T_3$ for 48 hours. The medians are shown as solid black lines within the box and the box indicates the $25^{th}$ and $75^{th}$ percentiles. Whiskers indicate the range. Greyed out regions indicate no detectable specific signal in the indicated tissue (refer to FIG. 8 for details). "a": signficantly different from the vehicle control group (p<0.05).

Figure 6:
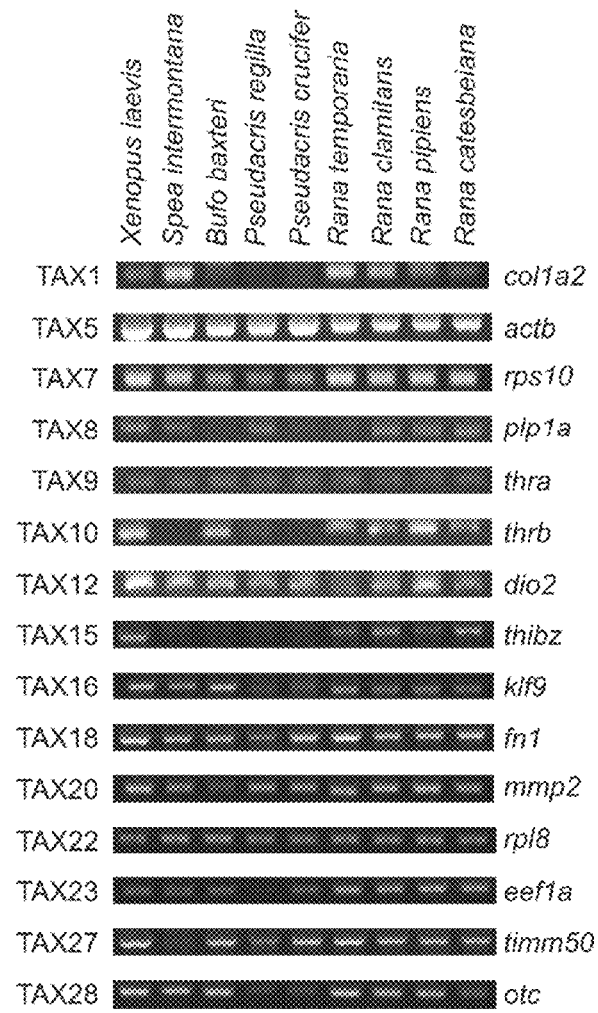
FIG. 6 illustrates results of tests demonstrating that primer sets according to an embodiment of the invention are usable in a wide range of Anuran species.

The primer sets can be used on multiple Anuran species beyond *Rana catesbeiana* and *Xenopus laevis*, as is demonstrated in FIG. 6. FIG. 6 illustrates a demonstration that the primer sets are usable in a wide range of anuran specifies. The primer sets in Table 1 were run on cDNA preparations made from a single tissue or mixture of tissues (species-dependent) on the indicated species to demonstrate that the appropriately sized amplicon is produced across a wide range of Anuran species.

Figure 7:
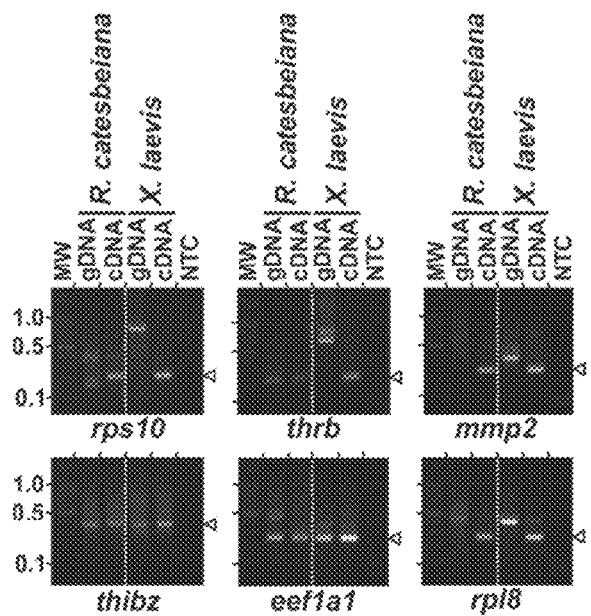
FIG. 7 are illustrations of representative examples of primer set performance on genomic DNA across different Anuran species.

Another use of the primers can be for detection of contaminating genomic DNA in transcriptomic studies or in amplification of genomic DNA (FIG. 7) and their utility in *Rana catesbeiana* and *Xenopus laevis* are summarized in Table 2. FIG. 7 illustrates representative examples of primer set performance on genomic DNA across different anuran species. Genomic DNA (gDNA) was isolated from skin of *Xenopus laevis* tadpoles and liver of *Rana catesbeiana* adults. For both species, complementary DNA (cDNA) was generated from total RNA isolated from mixed prometamorphic tadpole tissues. Location of the predicted PCR amplicon representative of expressed sequence for each gene target is shown by an arrowhead. MW denotes molecular size standards in kilobase pairs of linear DNA. The results for all of the primer sets are summarized in Table 2.

TABLE 2

Characterization of PCR amplified DNA products generated using genomic DNA of *Xenopus laevis* and *Rana catesbeiana* and the TAXISS primer panel[a] compared to amplicons generated from cDNA. The majority of primer sets amplify a distinctly different product or generate no product on genomic DNA from both species. This accentuates that, although the genomes of these species are very different, the ability to detect gDNA contamination in cDNA preparations is possible.

| TAXISS Primers | Gene Name | Rana catesbeiana | | | Xenopus laevis | | |
|---|---|---|---|---|---|---|---|
| | | Similar Product | Different Product | No Product | Similar Product | Different Product | No Product |
| TAX1 | col1a2 | + | | | + | | |
| TAX5 | actb | | + | | | + | |
| TAX7 | rps10 | | + | | | + | |
| TAX8 | plp1 | | + | | | + | |
| TAX9 | thra | | + | | | + | |
| TAX10 | thrb | + | | | | + | |
| TAX12 | dio2 | | + | | | + | |
| TAX15 | thibz | + | | | + | | |
| TAX16 | klf9 | | + | | + | | |
| TAX18 | fn1 | | + | | | | + |
| TAX20 | mmp2 | | + | | | + | |
| TAX22 | rpl8 | | + | | | + | |

TABLE 2-continued

Characterization of PCR amplified DNA products generated using genomic DNA of Xenopus laevis and Rana catesbeiana and the TAXISS primer panel[a] compared to amplicons generated from cDNA. The majority of primer sets amplify a distinctly different product or generate no product on genomic DNA from both species. This accentuates that, although the genomes of these species are very different, the ability to detect gDNA contamination in cDNA preparations is possible.

| TAXISS Primers | Gene Name | Rana catesbeiana | | | Xenopus laevis | | |
|---|---|---|---|---|---|---|---|
| | | Similar Product | Different Product | No Product | Similar Product | Different Product | No Product |
| TAX23 | eef1a1 | + | | | + | | |
| TAX27 | timm50 | | + | | | | + |
| TAX28 | otc | | + | | | + | |

[a] PCR were performed using qPCR-associated reagents and thermoprofile conditions. Genomic DNA and cDNA reactions were carried out concurrently for comparison. The annealing temperature was 60° C. for all reactions.
[b] Relative comparison of amplicon band migration on agarose gels comparing amplicons generated from gDNA versus cDNA.

Each primer pair can be used independently of each other. In one embodiment, the invention comprises use of a primer pair by itself to detect particular genes within an Anuran nucleic acid sample.

In another embodiment, two or more of any of the primer pairs listed in Table 1 may be used.

The normalizer gene panel would include two or more of the following primer pairs: actb, rps10, rpl8, and eef1a1. The end-user would then be able to use evaluation tools readily available to finalize the appropriateness of each reference gene.

The thyroid hormone responsive gene panel would include two or more of the following primer pairs: col1a2, plp1, thra, thrb, dio2, thibz, klf9, fn1, mmp2, otc and timm50.

The assay of the invention further comprises the following method. Tadpoles are exposed to the compound of interest in water and, at the appropriate time (e.g., within hours to a few days), two standardized portions of the tail are removed. The tail tips are immediately subjected to an apoptosis assay in Phase 1, while the other (second) tail portion is preserved for Phase 2.

If the results for Phase 1 are negative, then the substance is not thyroid axis active. No further analysis is necessary. If the Phase 1 results are positive, then the second tail portion is analyzed for shifts in the quantity of mRNA transcripts specifically identified for responsiveness in Phase 2. An example of Phase 2 analysis is using quantitative real time polymerase chain reaction (qPCR) for each gene transcript target.

If the gene transcripts indicative of thyroid hormone (TH) action are not affected, then it can be concluded that the test compound is not thyroid axis active. If the transcripts are affected, then the compound is identified as a likely TH disruptor.

Accordingly, disclosed herein is a frog tadpole metamorphosis assay method comprising a first phase and a second phase, wherein:

the first phase comprises exposing a tadpole to a compound of interest, removing first and second portions of the tadpole's tail, subjecting the first portion to an apatosis assay, and the second phase comprises subjecting the second portion to an assay to detect shifts in a quantity of pre-determined mRNA transcripts.

In a more specific embodiment of the method, the first phase further comprises determining whether the compound of interest is thyroid axis active.

In yet another embodiment of the method, the second phase further comprises subjecting the second portion to qPCR.

In still yet another embodiment, the first phase further comprises determining whether the compound of interest is thyroid axis active, and the second phase further comprises subjecting the second portion to qPCR.

In an embodiment of the invention, disclosed is a metamorphosis assay wherein the first phase comprises exposing a tadpole to a compound of interest, removing first and second portions of the tadpole's tail, and subjecting the first portion to an apatosis assay, and the second phase comprises subjecting the second portion to qPCR using a primer pair comprising a first primer and a second primer, wherein the primer pair is selected from the group consisting of primer pairs A, B, C, D, E, F, G, H, I, J, K, L, M, N, and O:

| Primer Pair | First Primer | SEQ ID NO: | Second Primer | SEQ ID NO: |
|---|---|---|---|---|
| A | CTGGTGGTGGAT ATGATGGT | 1 | GAGTCTTAAGTCA CGGCAAG | 2 |
| B | TACAGCTTCACC ACCACAG | 3 | TCCACATCTGCTG GAAGGT | 4 |
| C | TTTGCYTGGCGK CACTTTT | 5 | ARCRGCACTGCGY CTGTA | 6 |
| D | TGGCTGARGGAT TYTAYACC | 7 | ACAGCAGAGCAGG CAAMGA | 8 |
| E | TGATAAGGCCAC AGGRTACCACTA | 9 | CGGGTGATCTTGT CGATRA | 10 |
| F | CTCATAGAAGAA AACAGAGAAAAR AGA | 11 | GAAGGCTTCTAAG TCCACTTTTCC | 12 |
| G | CCTGGCTCTSTA YGACTC | 13 | RGCTGATCCRAAR TTGAC | 14 |
| H | ASCTCCRCAGAA YCAGCA | 15 | TCACGTACCAGGC CAAAA | 16 |
| I | CYGCTCAGTGTC TGGTGT | 17 | ARGGGCCGGTACT TGTTT | 18 |
| J | GTTGCCATGARG GWGGAC | 19 | CCATTGCCWGTGC AGATA | 20 |
| K | TACAACAGCTGC ACTGAT | 21 | TCCTTGTCATAGT CTTCTGT | 22 |

| Primer Pair | First Primer | SEQ ID NO: | Second Primer | SEQ ID NO: |
|---|---|---|---|---|
| L | CAGGGGACAGAG AAAAGGTG | 23 | TGAGCTTTCTTGC CACAG | 24 |
| M | GCTGCTGGTGTT GGTGART | 25 | AGCATGTTGTCAC CRTTCC | 26 |
| N | GCTWCAYCCAGA GTGGTCGTT | 27 | GCTGYTCCTCCTG CTCCA | 28 |
| O | YATGACYGATGC TGTTCTAG | 29 | CATAWCCCTTTGG TGTTGC | 30 |

In yet another particular embodiment of the invention, the second phase further comprises subjecting the second portion to qPCR using two or more primer pairs, wherein each pair comprises a first primer and a second primer, and the primer pairs are selected from the group consisting of primer pairs A, B, D, E, F, G, H, I, J, K, and O:

| Primer Pair | First Primer | SEQ ID NO: | Second Primer | SEQ ID NO: |
|---|---|---|---|---|
| A | CTGGTGGTGGAT ATGATGGT | 1 | GAGTCTTAAGTCA CGGCAAG | 2 |
| B | TACAGCTTCACC ACCACAG | 3 | TCCACATCTGCTG GAAGGT | 4 |
| D | TGGCTGARGGAT TYTAYACC | 7 | ACAGCAGAGCAGG CAAMGA | 8 |
| E | TGATAAGGCCAC AGGRTACCACTA | 9 | CGGGTGATCTTGT CGATRA | 10 |
| F | CTCATAGAAGAA AACAGAGAAAAR AGA | 11 | GAAGGCTTCTAAG TCCACTTTTCC | 12 |
| G | CCTGGCTCTSTA YGACTC | 13 | RGCTGATCCRAAR TTGAC | 14 |
| H | ASCTCCRCAGAA YCAGCA | 15 | TCACGTACCAGGC CAAAA | 16 |
| I | CYGCTCAGTGTC TGGTGT | 17 | ARGGGCCGGTACT TGTTT | 18 |
| J | GTTGCCATGARG GWGGAC | 19 | CCATTGCCWGTGC AGATA | 20 |
| K | TACAACAGCTGC ACTGAT | 21 | TCCTTGTCATAGT CTTCTGT | 22 |
| O | YATGACYGATGC TGTTCTAG | 29 | CATAWCCCTTTGG TGTTGC | 30 |

The invention further relates to a composition of matter comprising a primer pair selected from the group consisting of primer pairs A, B, C, D, E, F, G, H, I, J, K, L, M, N, and O:

| Primer Pair | First Primer | SEQ ID NO: | Second Primer | SEQ ID NO: |
|---|---|---|---|---|
| A | CTGGTGGTGGAT ATGATGGT | 1 | GAGTCTTAAGTCA CGGCAAG | 2 |
| B | TACAGCTTCACC ACCACAG | 3 | TCCACATCTGCTG GAAGGT | 4 |
| C | TTTGCYTGGCGK CACTTTT | 5 | ARCRGCACTGCGY CTGTA | 6 |
| D | TGGCTGARGGAT TYTAYACC | 7 | ACAGCAGAGCAGG CAAMGA | 8 |
| E | TGATAAGGCCAC AGGRTACCACTA | 9 | CGGGTGATCTTGT CGATRA | 10 |
| F | CTCATAGAAGAA AACAGAGAAAAR AGA | 11 | GAAGGCTTCTAAG TCCACTTTTCC | 12 |
| G | CCTGGCTCTSTA YGACTC | 13 | RGCTGATCCRAAR TTGAC | 14 |
| H | ASCTCCRCAGAA YCAGCA | 15 | TCACGTACCAGGC CAAAA | 16 |
| I | CYGCTCAGTGTC TGGTGT | 17 | ARGGGCCGGTACT TGTTT | 18 |
| J | GTTGCCATGARG GWGGAC | 19 | CCATTGCCWGTGC AGATA | 20 |
| K | TACAACAGCTGC ACTGAT | 21 | TCCTTGTCATAGT CTTCTGT | 22 |
| L | CAGGGGACAGAG AAAAGGTG | 23 | TGAGCTTTCTTGC CACAG | 24 |
| M | GCTGCTGGTGTT GGTGART | 25 | AGCATGTTGTCAC CRTTCC | 26 |
| N | GCTWCAYCCAGA GTGGTCGTT | 27 | GCTGYTCCTCCTG CTCCA | 28 |
| O | YATGACYGATGC TGTTCTAG | 29 | CATAWCCCTTTGG TGTTGC | 30 |

Yet another aspect of the invention relates to a normalizer gene panel comprising two or more primer pairs selected from the group consisting of primer pairs B, C, L, and M:

| Primer Pair | First Primer | SEQ ID NO: | Second Primer | SEQ ID NO: |
|---|---|---|---|---|
| B | TACAGCTTCACC ACCACAG | 3 | TCCACATCTGCTG GAAGGT | 4 |
| C | TTTGCYTGGCGK CACTTTT | 5 | ARCRGCACTGCGY CTGTA | 6 |
| L | CAGGGGACAGAG AAAAGGTG | 23 | TGAGCTTTCTTGC CACAG | 24 |
| M | GCTGCTGGTGTT GGTGART | 25 | AGCATGTTGTCAC CRTTCC | 26 |

Yet another aspect of the invention relates to a thyroid hormone responsive gene panel comprising two or more primer pairs selected from the group consisting of primer pairs A, D, E, F, G, H, I, J, K, N and O:

| Primer Pair | First Primer | SEQ ID NO: | Second Primer | SEQ ID NO: |
|---|---|---|---|---|
| A | CTGGTGGTGGAT ATGATGGT | 1 | GAGTCTTAAGTCA CGGCAAG | 2 |

-continued

| Primer Pair | First Primer | SEQ ID NO: | Second Primer | SEQ ID NO: |
|---|---|---|---|---|
| D | TGGCTGARGGAT TYTAYACC | 7 | ACAGCAGAGCAGG CAAMGA | 8 |
| E | TGATAAGGCCAC AGGRTACCACTA | 9 | CGGGTGATCTTGT CGATRA | 10 |
| F | CTCATAGAAGAA AACAGAGAAAAR AGA | 11 | GAAGGCTTCTAAG TCCACTTTTCC | 12 |
| G | CCTGGCTCTSTA YGACTC | 13 | RGCTGATCCRAAR TTGAC | 14 |
| H | ASCTCCRCAGAA YCAGCA | 15 | TCACGTACCAGGC CAAAA | 16 |
| I | CYGCTCAGTGTC TGGTGT | 17 | ARGGGCCGGTACT TGTTT | 18 |
| J | GTTGCCATGARG GWGGAC | 19 | CCATTGCCWGTGC AGATA | 20 |
| K | TACAACAGCTGC ACTGAT | 21 | TCCTTGTCATAGT CTTCTGT | 22 |
| N | GCTWCAYCCAGA GTGGTCGTT | 27 | GCTGYTCCTCCTG CTCCA | 28 |
| O | YATGACYGATGC TGTTCTAG | 29 | CATAWCCCTTTGG TGTTGC | 30 |

LITERATURE CITED

AmphibiaWeb. (2012). "AmphibiaWeb: Information on amphibian biology and conservation." Retrieved Jan. 12, 2012, from www.amphibiaweb.org.

Bernal, J. (2005). "Thyroid hormones and brain development." *Vitamins and Hormones* 71: 95-122.

Brucker-Davis, F. (1998). "Effects of environmental synthetic chemicals on thyroid function." *Thyroid* 8: 827-856.

Bruno, J. (2001). Toxicity test using premetamorphic bullfrog tadpoles (*Rana catesbeiana*). North Vancouver, Pacific Environmental Sciences Centre: 1-9.

Bustin, S. A., J. F. Beaulieu, et al. (2010). "MIQE precis: Practical implementation of minimum standard guidelines for fluorescence-based quantitative real-time PCR experiments." *BMC Mol Biol* 11:74.

Cheng, S.-Y. (2005). "Thyroid hormone receptor mutations and disease: beyond thyroid hormone resistance." *Trends in Endocrinology and Metabolism* 16: 176-182.

Hecker, M. and H. Hollert (2011). "Endocrine disruptor screening: regulatory perspectives and needs." *Environ Sci Europe* 23:15.

Helbing, C. C. (2012). "The metamorphosis of amphibian toxicogenomics." *Front Genet* 3: 37.

Jones, S., K. Thoemke, et al. (2005). "The role of thyroid hormone in fetal and neonatal brain development." *Current Opinion in Endocrinology and Diabetes* 12: 10-16.

Kolpin, D., E. Furlong, et al. (2002). "Pharmaceuticals, hormones, and other organic wastewater contaminants in US streams, 1999-2000: A national reconnaissance." *Environmental Science and Technology* 36: 1202-1211.

Liu, Y. Y. and G. A. Brent (2010). "Thyroid hormone crosstalk with nuclear receptor signaling in metabolic regulation." *Trends Endocrinol Metab* 21(3): 166-173.

Marlatt, V. L., N. Veldhoen, et al. (2013). "Triclosan exposure alters postembryonic development in a Pacific tree frog (Pseudacris regilla) Amphibian Metamorphosis Assay (TREEMA)." *Aquat Toxicol* 126: 85-94.

Miller, M. D., K. M. Crofton, et al. (2009). "Thyroid-disrupting chemicals: interpreting upstream biomarkers of adverse outcomes." *Environ Health Perspect* 117(7): 1033-1041.

Mitsui, N., T. Fujii, et al. (2006). "Development of metamorphosis assay using *Silurana tropicalis* for the detection of thyroid system-disrupting chemicals." *Ecotoxicology and Environmental Safety* 64(3): 281-287.

Morreale de Escobar, G., M. Obregon, et al. (2004). "Role of thyroid hormone during early brain development." *Eur J Endocrinol* 151: U25-U37.

NIEHS. (2013). "About the NTP." Retrieved Feb. 2, 2013, from ntp.niehs.nih.gov.

OECD (2009). "OECD Guideline for the testing of chemicals Test No. 231: The Amphibian Metamorphosis Assay."

Oka, T., M. Miyahara, et al. (2009). "Application of metamorphosis assay to a native Japanese amphibian species, *Rana rugosa*, for assessing effects of thyroid system affecting chemicals." *Ecotoxicology and Environmental Safety* 72(5): 1400-1405.

Porterfield, S. (1994). "Vulnerability of the developing brain to thyroid abnormalities: environmental insults to the thyroid system." *Environmental Health Perspectives* 102: 125-130.

Quanrud, D. and C. Propper (2010). Wastewater effluent: Biological impacts of exposure and treatment processes to reduce risk, Nature Conservancy, Arizona.

Relyea, R. A. and D. K. Jones (2009). "The Toxicity of Roundup Original Max® to 13 Species of Larval Amphibians." *Environmental Toxicology and Chemistry* 28(9): 2004-2008.

Searcy, B. T., S. M. Beckstrom-Sternberg, et al. (2012). "Thyroid hormone-dependent development in *Xenopus laevis*: a sensitive screen of thyroid hormone signaling disruption by municipal wastewater treatment plant effluent." *Gen Comp Endocrinol* 176(3): 481-492.

Shi, Y.-B. (2000). Amphibian Metamorphosis: From morphology to molecular biology. New York, Wiley-Liss.

Siesser, W. B., S.-Y. Cheng, et al. (2005). "Hyperactivity, impaired learning on a vigilance task, and a differential response to methylphenidate in the TR-PV knock-in mouse." *Psychopharmacology* 181: 653-663.

Sumida, M., Y. Kato, et al. (2004). "Sequencing and analysis of the internal transcribed spacers (ITSs) and coding regions in the EcoR I fragment of the ribosomal DNA of the Japanese pond frog *Rana nigromaculata.*" *Genes & Genetic Systems* 79(2): 105-118.

Van Aggelen, G., G. T. Ankley, et al. (2010). "Integrating omic technologies into aquatic ecological risk assessment and environmental monitoring: hurdles, achievements, and future outlook." *Environ Health Perspect* 118(1): 1-5.

Vandenberg, L. N., T. Colborn, et al. (2012). "Hormones and endocrine-disrupting chemicals: Low-dose effects and nonmonotonic dose responses." *Endocr Rev* 33: doi: 10.1210/er.2011-1050.

Veldhoen, N., R. Skirrow, et al. (2006). "The bactericidal agent triclosan modulates thyroid hormone-associated gene expression and disrupts postembryonic anuran development." *Aquatic Toxicology* 80: 217-227.

Zoeller, R. (2005). "Environmental chemicals as thyroid hormone analogues: New studies indicate that thyroid hormone receptors are targets of industrial chemicals." *Molecular and Cellular Endocrinology* 242: 10-15.

Zoeller, R. and K. Crofton (2005). "Mode of action: developmental thyroid hormone insufficiency-neurological abnormalities resulting from exposure to propylthiouracil." *Crit Rev Toxicol* 35: 771-781.

Zoeller, R. and J. Rovett (2004). "Timing of thyroid hormone action in the developing brain: clinical observations and experimental findings." *Journal of Neuroendocrinology* 16: 809-818.

---

The invention claimed is:

1. A method for detecting changes in gene expression of thyroid hormones utilizing a frog tadpole metamorphosis assay method comprising a first phase and a second phase, wherein:
the first phase comprises exposing a tadpole to a compound of interest, removing first and second portions of the tadpole's tail, subjecting the first portion to an apoptosis assay, and
the second phase comprises subjecting the second portion to an assay to detect shifts in a quantity of pre-determined mRNA transcripts, wherein the second phase further comprises subjecting the second portion to qPCR using a primer pair comprising a first primer and a second primer, wherein the primer pair is selected from the group consisting of primer pairs A, D, E, F, G, H, I, J, K, N and O:

| Primer Pair | First Primer | SEQ ID NO: | Second Primer | SEQ ID NO: |
|---|---|---|---|---|
| A | CTGGTGGTGGAT ATGATGGT | 1 | GAGTCTTAAGTCA CGGCAAG | 2 |
| D | TGGCTGARGGAT TYTAYACC | 7 | ACAGCAGAGCAGG CAAMGA | 8 |
| E | TGATAAGGCCAC AGGRTACCACTA | 9 | CGGGTGATCTTGT CGATRA | 10 |
| F | CTCATAGAAGAA AACAGAGAAAAR AGA | 11 | GAAGGCTTCTAAG TCCACTTTTCC | 12 |
| G | CCTGGCTCTSTA YGACTC | 13 | RGCTGATCCRAAR TTGAC | 14 |
| H | ASCTCCRCAGAA YCAGCA | 15 | TCACGTACCAGGC CAAAA | 16 |
| I | CYGCTCAGTGTC TGGTGT | 17 | ARGGGCCGGTACT TGTTT | 18 |
| J | GTTGCCATGARG GWGGAC | 19 | CCATTGCCWGTGC AGATA | 20 |
| K | TACAACAGCTGC ACTGAT | 21 | TCCTTGTCATAGT CTTCTGT | 22 |
| N | GCTWCAYCCAGA GTGGTCGTT | 27 | GCTGYTCCTCCTG CTCCA | 28 |
| O | YATGACYGATGC TGTTCTAG | 29 | CATAWCCCTTTGG TGTTGC. | 30 |

2. The assay method of claim 1, wherein the first phase further comprises determining whether the compound of interest is thyroid axis active.

3. The assay method of claim 1, wherein the second phase further comprises subjecting the second portion to qPCR using two or more primer pairs.

4. A method for detecting changes in gene expression of thyroid hormones utilizing a frog tadpole metamorphosis assay method, comprising the steps of:
exposing a tadpole to a compound of interest; and
subjecting a tail portion of said tadpole to an assay to detect shifts in a quantity of pre-determined mRNA transcripts, wherein said assay comprises subjecting the portion to qPCR using a primer pair comprising a first primer and a second primer, wherein the primer pair is selected from the group consisting of primer pairs A, D, E, F, G, H, I, J, K, N and O:

| Primer Pair | First Primer | SEQ ID NO: | Second Primer | SEQ ID NO: |
|---|---|---|---|---|
| A | CTGGTGGTGGAT ATGATGGT | 1 | GAGTCTTAAGTCA CGGCAAG | 2 |
| D | TGGCTGARGGAT TYTAYACC | 7 | ACAGCAGAGCAGG CAAMGA | 8 |
| E | TGATAAGGCCAC AGGRTACCACTA | 9 | CGGGTGATCTTGT CGATRA | 10 |
| F | CTCATAGAAGAA AACAGAGAAAAR AGA | 11 | GAAGGCTTCTAAG TCCACTTTTCC | 12 |
| G | CCTGGCTCTSTA YGACTC | 13 | RGCTGATCCRAAR TTGAC | 14 |
| H | ASCTCCRCAGAA YCAGCA | 15 | TCACGTACCAGGC CAAAA | 16 |
| I | CYGCTCAGTGTC TGGTGT | 17 | ARGGGCCGGTACT TGTTT | 18 |
| J | GTTGCCATGARG GWGGAC | 19 | CCATTGCCWGTGC AGATA | 20 |
| K | TACAACAGCTGC ACTGAT | 21 | TCCTTGTCATAGT CTTCTGT | 22 |
| N | GCTWCAYCCAGA GTGGTCGTT | 27 | GCTGYTCCTCCTG CTCCA | 28 |
| O | YATGACYGATGC TGTTCTAG | 29 | CATAWCCCTTTGG TGTTGC. | 30 |

* * * * *

SEQUENCE LISTING

```
<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctggtggtgg atatgatggt                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gagtcttaag tcacggcaag                                              20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tacagcttca ccaccacag                                               19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tccacatctg ctggaaggt                                               19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttgcytggc gkcactttt                                               19
```

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
arcrgcactg cgyctgta                                                 18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
tggctgargg attytayacc                                               20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
acagcagagc aggcaamga                                                19

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
tgataaggcc acaggrtacc acta                                          24

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
cgggtgatct tgtcgatra                                                19

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
ctcatagaag aaaacagaga aaaraga                                       27

-continued

```
<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaaggcttct aagtccactt ttcc                                            24

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cctggctcts taygactc                                                   18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
rgctgatccr aarttgac                                                   18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
asctccrcag aaycagca                                                   18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcacgtacca ggccaaaa                                                   18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cygctcagtg tctggtgt                                                   18
```

```
<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
argggccggt acttgttt                                                 18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gttgccatga rggwggac                                                 18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccattgccwg tgcagata                                                 18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tacaacagct gcactgat                                                 18

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tccttgtcat agtcttctgt                                               20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caggggacag agaaaaggtg                                               20
```

```
<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgagctttct tgccacag                                                      18

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gctgctggtg ttggtgart                                                     19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agcatgttgt caccrttcc                                                     19

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gctwcaycca gagtggtcgt t                                                  21

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gctgytcctc ctgctcca                                                      18

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
yatgacygat gctgttctag                                                    20
```

```
<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
catawccctt tggtgttgc                                                 19
```